(12) United States Patent
Lin et al.

(10) Patent No.: US 11,243,198 B2
(45) Date of Patent: Feb. 8, 2022

(54) GAS SENSING DEVICE AND GAS CONCENTRATION SENSING METHOD

(71) Applicant: INDUSTRIAL TECHNOLOGY RESEARCH INSTITUTE, Hsinchu (TW)

(72) Inventors: Yu-Ying Lin, Tainan (TW); Ying-Che Lo, Tainan (TW); Chung-Yi Hsu, Tainan (TW); Po-Jen Su, Tainan (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 53 days.

(21) Appl. No.: 16/879,340

(22) Filed: May 20, 2020

(65) Prior Publication Data
US 2021/0190744 A1    Jun. 24, 2021

(30) Foreign Application Priority Data
Dec. 20, 2019  (TW) ................................. 108147004

(51) Int. Cl.
*G01N 33/00* (2006.01)
*G01N 27/12* (2006.01)

(52) U.S. Cl.
CPC ......... *G01N 33/0006* (2013.01); *G01N 27/12* (2013.01); *G01N 33/0036* (2013.01)

(58) Field of Classification Search
CPC ............. G01N 33/4972; G01N 33/497; G01N 2033/4975; G01N 33/0006;
(Continued)

(56) References Cited

U.S. PATENT DOCUMENTS

| 4,347,732 A | 9/1982 | Leary |
| 4,792,433 A * | 12/1988 | Katsura ................. G01N 27/12 324/71.5 |

(Continued)

FOREIGN PATENT DOCUMENTS

| CN | 108896641 A | 11/2018 |
| CN | 110520727 A | 11/2019 |

(Continued)

OTHER PUBLICATIONS

Schüler et al. "A novel approach for detecting HMDSO poisoning of metal oxide gas sensors and improving their stability by temperature cycled operation" J. Sens. Sens. Syst., 4, 305-311, Oct. 19, 2015.

(Continued)

*Primary Examiner* — David A. Rogers
(74) *Attorney, Agent, or Firm* — Maschoff Brennan

(57) ABSTRACT

A gas sensing device is adapted to detect a concentration of a target gas. The gas sensing device comprises a dielectric layer, a reference sensing portion, a target sensing portion, and a controller. The dielectric layer is disposed on a surface. The reference sensing portion and the target sensing portion are respectively disposed on a supporting side of the dielectric layer, with said supporting side facing away from the surface. The reference sensing portion includes a first conductive layer and a first sensing layer with low sensitivity to the target gas. The target sensing portion includes a second conductive layer and a second sensing layer with high sensitivity to the target gas. The controller obtains the immittance values of the first conductive layer and the second conductive layer, and calculates a concentration value of the target gas according to the immittance values and a correlation function.

28 Claims, 16 Drawing Sheets

100

(58) Field of Classification Search
CPC ............. G01N 33/0031; G01N 33/004; G01N 33/0037; G01N 33/0039; G01N 33/0042; G01N 33/0044; G01N 33/005; G01N 33/0052
See application file for complete search history.

(56) References Cited

U.S. PATENT DOCUMENTS

| | | | |
|---|---|---|---|
| 5,844,122 A | 12/1998 | Kato | |
| 7,846,320 B2* | 12/2010 | Tice | G01N 33/0006 205/775 |
| 10,571,420 B2* | 2/2020 | Samarao | C23C 16/45525 |
| 10,908,138 B2* | 2/2021 | Motayed | G01N 33/0047 |
| 2006/0267051 A1 | 11/2006 | Gstrein et al. | |
| 2009/0126454 A1 | 5/2009 | Pratt et al. | |
| 2014/0238100 A1 | 8/2014 | Londergan et al. | |
| 2016/0187279 A1 | 6/2016 | Tayebi et al. | |
| 2017/0299536 A1 | 10/2017 | Tsuboi et al. | |
| 2018/0299404 A1 | 10/2018 | Nunome et al. | |
| 2019/0145929 A1 | 5/2019 | Carbonelli et al. | |
| 2020/0033309 A1* | 1/2020 | Yuan | G01N 33/0013 |
| 2021/0003525 A1 | 1/2021 | Kaita et al. | |
| 2021/0132014 A1* | 5/2021 | Goel | G01N 33/004 |
| 2021/0262975 A1* | 8/2021 | Wakamori | G01N 27/4141 |

FOREIGN PATENT DOCUMENTS

| | | |
|---|---|---|
| EP | 3203229 A2 | 8/2017 |
| JP | S58-102141 A | 6/1983 |
| JP | S6014148 A | 1/1985 |
| JP | H6-11471 A | 1/1994 |
| JP | H8-170953 A | 7/1996 |
| JP | H11-160266 A | 6/1999 |
| JP | 2019069848 A | 4/2019 |
| TW | I588481 B | 10/2016 |
| TW | I603068 B | 10/2017 |
| WO | 2004011924 A | 2/2004 |

OTHER PUBLICATIONS

Abidin et al. "Comparative Study of Drift Compensation Methods for Environmental Gas Sensors" IOP Conference Series: Earth and Environmental Science 117; Feb. 1, 2018.
Burgués et al. "Low Power Operation of Temperature-Modulated Metal Oxide Semiconductor Gas Sensors" Sensors (Basel) Jan. 25, 2018.
Rüffer et al. "New Digital Metal-Oxide (MOx) Sensor Platform" Sensors, 18, 1052; Mar. 31, 2018.
Tournier et al. "Selective filter for SnO2-based gas sensor: Application to hydrogen trace detection" Sensors and Actuators B: Chemical; vol. 106, Issue 2, May 13, 2005, pp. 553-562.
Williams "Semiconducting oxides as gas-sensitive resistors" Sensors and Actuators B 57 (1999) 1-16.
EP Search Report in Application No. 20184615.1 dated Jan. 29, 2021.

\* cited by examiner

GAS SENSING DEVICE AND GAS CONCENTRATION SENSING METHOD

CROSS-REFERENCE TO RELATED APPLICATIONS

This non-provisional application claims priority under 35 U.S.C. § 119(a) on Patent Application No(s). 108147004 filed in Taiwan, R.O.C. on Dec. 20, 2019, the entire contents of which are hereby incorporated by reference.

BACKGROUND

1. Technical Field

The present disclosure is adapted to sense a target gas, and more particularly to a gas sensing device with automatic calibration and calibration method thereof.

2. Related Art

Gas sensing devices are widely used in wearable devices and portable products, and are developed in the direction of miniaturization, low power consumption, high sensitivity and high stability.

The metal Oxide (MOX) gas sensing device uses a heater to heat the sensing material. The resistance of the sensing material increases when oxygen is adsorbed thereon. When the target gas reacts with oxygen ions adsorbed on the surface of the sensing material, the desorption of oxygen ions reduces the resistance of the sensing material, so the concentration value of the target gas can be estimated by detecting the resistance value of the sensing material.

However, since the variation of temperature or humidity in the environment leads to the unstable oxygen adsorption easily, and the sensing material is also susceptible to siloxane poisoning so that the oxygen adsorption sites are occupied, the above situation will cause a variation of the initial resistance of the sensing material. In addition, the sensitivity of the gas sensing device may also be affected by factors, such as the aging of the sensing material, the incomplete burn-in of the sensing device, and the aforementioned siloxane poisoning. In short, when using a MOX gas sensing device to detect the concentration of a target gas, the initial resistance and sensitivity of the gas sensing device will affect the detection accuracy due to environmental factors or time factors.

SUMMARY

According to an embodiment of the present disclosure, a gas concentration sensing method, adapted to a gas sensing device capable of sensing a concentration of a target gas in a gas under test, wherein the gas sensing device comprises a reference sensing portion, a target sensing portion, and a controller, a sensitivity of the reference sensing portion to the target gas is lower than a sensitivity of the target sensing portion to the target gas, and the gas concentration sensing method comprises: detecting a measured reference immittance value of the reference sensing portion and a measured target immittance value of the target sensing portion by the controller when the reference sensing portion and the target sensing portion are in contact with the gas under test; calculating a reference coefficient of variation by the controller according to the measured reference immittance value and an initial reference immittance value corresponding to the reference sensing portion; and calculating a target gas concentration value by the controller according to the reference coefficient of variation, a correlation function, the measured target immittance value, and a target gas concentration converting function, wherein the correlation function represents a correlation between the reference sensing portion and the target sensing portion.

According to an embodiment of the present disclosure, a gas concentration sensing method adapted to a gas sensing device capable of sensing a concentration of a target gas in a gas under test, wherein the gas sensing device comprises a reference sensing portion, a target sensing portion, and a controller, a sensitivity of the reference sensing portion to the target gas is lower than a sensitivity of the target sensing portion to the target gas, and the gas concentration sensing method comprises: an immittance obtaining stage comprising detecting a measured reference immittance value of the reference sensing portion and a measured target immittance value of the target sensing portion when the reference sensing portion and the target sensing portion are in contact with the gas under test; a range calculating stage comprising calculating a plurality of predicted target immittance values according to the measured reference immittance value and a plurality of correlation functions by the controller, with both the plurality of correlation functions and the plurality of predicted target immittance values corresponding to a plurality of specified concentration values; a range comparing stage comprising comparing the measured target immittance value to the plurality of predicted target immittance values by the controller for selecting one of the plurality of specified concentration values; and a concentration calculating stage comprising calculating a target gas concentration value according to one of a plurality of target coefficients of variation and the measured target immittance value by the controller, with said one of the plurality of target coefficients of variation corresponding to said one of the plurality of specified concentration values.

According to an embodiment of the present disclosure, a gas concentration sensing method adapted to a gas sensing device capable of sensing a concentration of a target gas in a gas under test, wherein the gas sensing device comprises a first reference sensing portion, a second reference sensing portion, a target sensing portion, and a controller, both a sensitivity of the first reference sensing portion to the target gas and a sensitivity of the second reference sensing portion to the target gas are lower than a sensitivity of the target sensing portion to the target gas, and the gas concentration sensing method comprises: an immittance obtaining stage comprising detecting a first measured reference immittance value of the first reference sensing portion, a second measured reference immittance value of the second reference sensing portion, and a measured target immittance value of the target sensing portion when the reference sensing portion and the target sensing portion are in contact with the gas under test; a range calculating stage comprising calculating a plurality of range reference values according to the first measured reference immittance value, the second measured reference immittance value, and a plurality of correlation functions by the controller, with both the plurality of correlation functions and the plurality of range reference values corresponding to a plurality of specified concentration values; a range comparing stage comprising comparing the plurality of range reference values to a comparison baseline value by the controller for selecting one of the plurality of specified concentration values; and a concentration calculating stage comprising calculating a target gas concentration value according to a target coefficient of variation and the measured target immittance value by the controller, with the target coefficient of variation corresponding to said one of the plurality of specified concentration values.

According to an embodiment of the present disclosure, a gas sensing device capable of sensing a concentration of a target gas in a gas under test comprising: a dielectric layer disposed on a surface, wherein the dielectric layer has a supporting side facing away from the surface; a reference sensing portion disposed on the supporting side, wherein the reference sensing portion comprises a first sensing layer and a first conductive layer; a target sensing portion disposed on the supporting side, wherein the target sensing portion comprises a second sensing layer and a second conductive layer; and a controller electrically connecting to the first conductive layer and the second conductive layer, wherein the controller detects a measured reference immittance value of the first conductive layer and a measured target immittance value of the second conductive layer and calculates a target gas concentration value of the target gas according to an initial reference immittance value, a correlation function associated with the reference sensing portion and the target sensing portion, the measured reference immittance value and the measured target immittance value; wherein a sensitivity of the reference sensing portion to the target gas is lower than a sensitivity of the target sensing portion to the target gas.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. The following examples further illustrate the perspective of the present disclosure in detail, but these examples should not be viewed as limitations of the present disclosure.

The present disclosure proposes a gas sensing device and a gas concentration sensing method. In the following, a first embodiment of the gas sensing device is described first, then two examples of the gas concentration sensing method adapted to the first embodiment of the gas sensing device; then second embodiment of the gas sensing device, and then four examples of the gas concentration sensing method adapted to the second embodiment of the gas sensing device is described.

Figure 1:
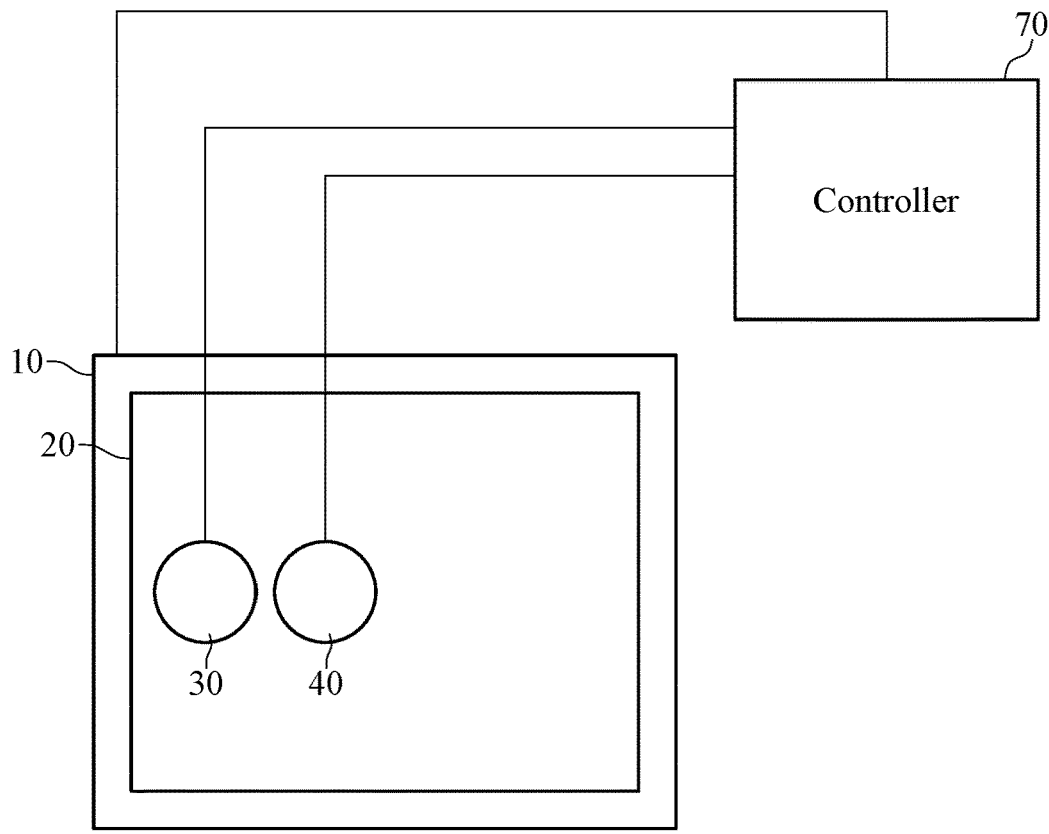
FIG. 1 is an architecture diagram of the gas sensing device of the first embodiment of the present disclosure.
Figure 2:
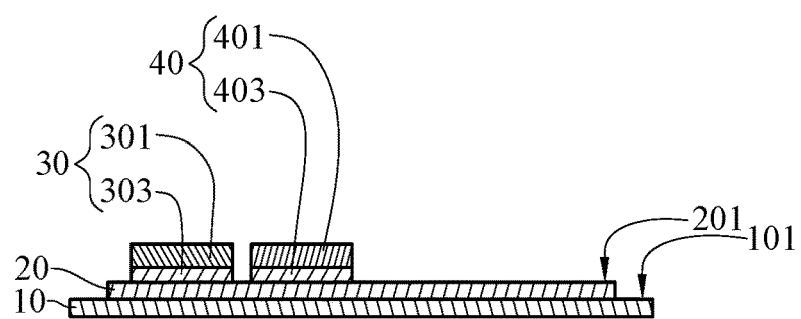
FIG. 2 is a side view of the heater, the dielectric layer, the reference sensing portion, and the target sensing portion.

Please refer to FIG. 1, which illustrates an architecture diagram of the gas sensing device 100 of the first embodiment of the present disclosure. The gas sensing device 100 is capable of sensing a concentration of a target gas in a gas under test. The gas sensing device 100 includes a heater 10, a dielectric layer 20, a reference sensing portion 30, a target sensing portion 40, and a controller 70. Please refer to FIG. 2, which illustrates a side view of elements including the heater 10, the dielectric layer 20, the reference sensing portion 30, and the target sensing portion 40.

For example, the heater 10 may receive the power from an external power source (not depicted) through the controller 70. The heater 10 generates heat on its surface 101. For example, the heater 10 has a single heating element to heat the reference sensing portion 30 and the target sensing portion 40 together. For another example, the heater 10 has multiple heating elements to heat the reference sensing portion 30 and the target sensing portion 40 respectively. The purpose of disposing the heater 10 is to heat both the reference sensing portion 30 and the target sensing portion 40 to the same temperature at the same time, and the present disclosure does not limit the number of heating elements of the heater 10 as long as the purpose is achieved. In addition, the installation of the heater 10 may be neglected when the sensing material used by the reference sensing portion 30 and the target sensing portion 40 does not need to be heated, in other words, the target gas in the gas under test can be sensed at the room temperature, or the ambient temperature has reached the working temperature of the sensing material. The present disclosure is not limited to whether the heater 10 is provided.

The dielectric layer 20 is disposed on the surface 101 of the heater 10. The dielectric layer 20 has a supporting side 201. The supporting side 201 preferably faces away from the surface 101 of the heater 10. Both the reference sensing portion 30 and the target sensing portion 40 are disposed on the supporting side 201.

The reference sensing portion 30 includes a first sensing layer 301 and a first conductive layer 303. The first sensing layer 301 is a metal oxide, and is low sensitive to the target gas. The first conductive layer 303 connects to the first sensing layer 301 so that the current transmitted by the first conductive layer 303 may flow through the first sensing layer 301. Therefore, the controller 70 may detect an immittance value of the first conductive layer 303, and this immittance value, such as the resistance value or the conductance value for direct current, is called "measured reference immittance value" hereafter. For the convenience of illustration, resistance values are preferred as examples of the immittance value in the following content. Disposing the reference sensing portion 30 is to reflect the current environment such as the humidity in the air for subsequent correction to the detected immittance value of the metal oxide due to the influence of environmental factors.

The target sensing portion 40 includes a second sensing layer 401 and a second conductive layer 403. The second sensing layer 401 is a metal oxide, and is high sensitive to the target gas. The second conductive layer 403 connects to the second sensing layer 401 so that the current transmitted by the second conductive layer 403 may flow through the second sensing layer 401. Therefore, the controller 70 may detect an immittance value of the second conductive layer 403. Similarly, this immittance value is called "measured target immittance value" hereafter. For the convenience of illustration, resistance values are preferred as examples of the immittance value in the following content. The purpose of disposing the target sensing portion 40 is to sense the concentration of the target gas when the metal oxide is in contact with the gas under test by detecting the immittance value of the metal oxide of target sensing portion 40. In addition, the gas sensing device 100 may further include another target sensing portion as a backup when the target sensing portion 40 is broken. In this situation, the heating operations on this two target sensing portions by the heater 10 are unrelated, and the heating operations may be performed either at the same time or not.

In this specification, the definition of "low sensitivity" is that a sensitivity of the reference sensing portion 30 to the target gas is lower than a sensitivity of the target sensing portion 40 to the target gas. Deposition with a specific metal may be adopted in order to adjust the sensitivity of the sensing material to the target gas. For example, sensing materials, such as tungsten oxide ($WO_3$) and tin oxide ($SnO_2$), may be deposited in the supporting side 201 of the dielectric layer 20. The deposition method is "drop coating" or "sputtering deposition". The portion of the supporting side 201 deposited with tungsten oxide may be served as the first sensing layer 301 of the reference sensing portion 30, wherein the particle size of the sensing material is 30 nanometers and the thickness is 0.1 micrometers. The portion of the supporting side 201 deposited with tin oxide may be served as the second sensing layer 401 of the target sensing portion 40, wherein the particle size of the sensing material is 7-10 nanometers and the thickness is 1 micrometer. The present disclosure does not limit the area and the kind of the deposited sensing material of the first sensing layer 301 and the second sensing layer 401, and does not limit the area and the thickness of the first conductive layer 303 and the second conductive layer 403. Regarding the sensing portion with low sensitivity and the sensing portion with high sensitivity, the larger a difference between said high and low sensitivities to the target gas is, the more preferable the sensing portions with these sensitivities are. In other words, it is preferable that the sensitivity of the reference sensing portion 30 to the target gas is low, and the best case is non-sensitivity. On the other hand, it is preferable that the sensitivity of the target sensing portion 40 to the target gas is large.

Please refer to FIG. 1. The controller 70 electrically connects to the heater 10, the reference sensing portion 30 and the target sensing portion 40. For example, the controller 70 further includes a heating driver (not depicted) configured to drive one or more heating elements of the heater 10. When the heater 10 heats the reference sensing portion 30 and the target sensing portion 40 and the gas under test is directed to the gas sensing device 100, the controller 70 detects the measured reference immittance value of the reference sensing portion 30 and the measured target immittance value of the target sensing portion 40. In addition, the controller 70 is configured to obtain at least one of a plurality of default data. Therefore, the controller 70 may calculate the concentration value of the target gas in the gas under test according to the measured reference immittance value, the measured target immittance value, and the default data.

Regarding the storage of the default data, for example, a built-in storage element of the controller 70 may be adopted. For another example, a storage device outside the controller 70 may be adopted. This storage device communicably connects to the controller 70 so that the controller 70 may obtain the default data.

Said default data includes a plurality of initial reference resistance values (initial reference immittance values) associated with the reference sensing portion 30, a plurality of initial target resistance values (initial target immittance values) associated with the target sensing portion 40, a plurality of specified concentration values, a plurality of correlation functions associated with the reference sensing portion 30 and the target sensing portion 40, and at least one target gas concentration converting function. The specific contents of each of the default data will be described along with the examples of the gas concentration sensing method of the present disclosure.

Figure 3A:
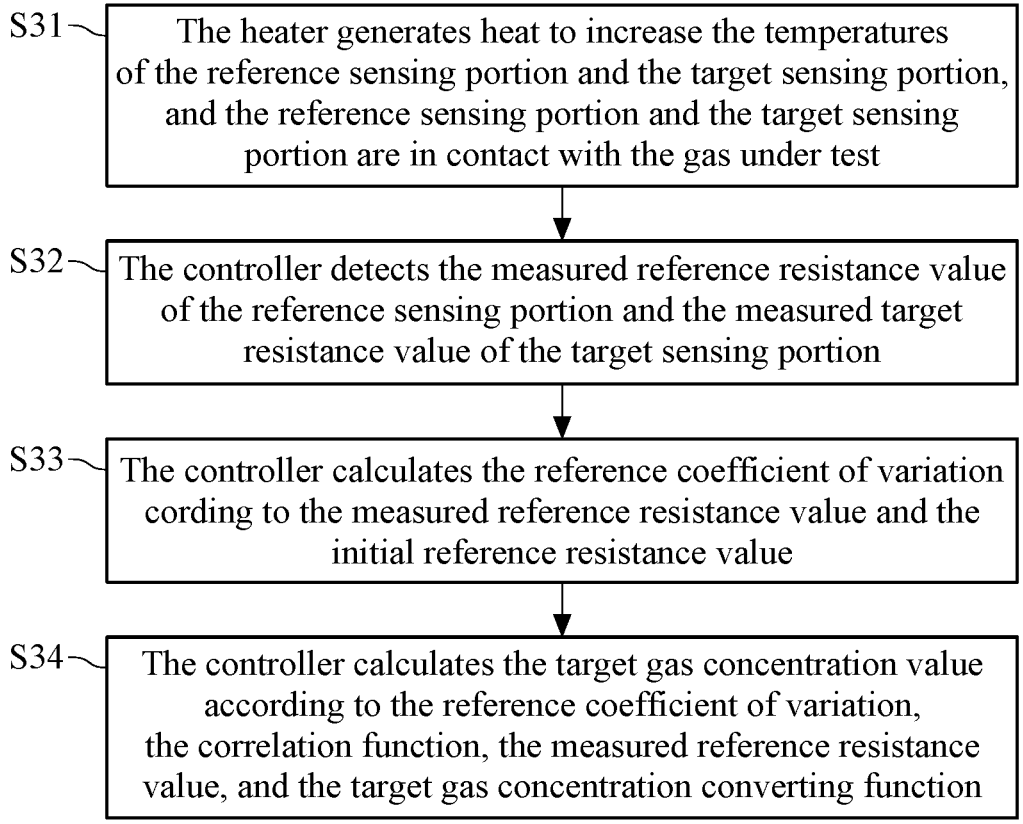
FIG. 3A is a flowchart of the gas concentration sensing method of the first example of the present disclosure.

Please refer to FIG. 3A, which illustrates a flowchart of the gas concentration sensing method of the first example of the present disclosure. The gas concentration sensing method is adapted to the gas sensing device 100 capable of sensing the target gas as described in this embodiment. Said gas sensing device 100 includes the heater 10, the reference sensing portion 30 low sensitive to the target gas, the target sensing portion 40 high sensitive to the target gas and the controller 70. It should be noticed that although what obtained by the reference sensing portion 30 and the target sensing portion 40 in the following steps are resistance values, they are merely examples and may be implemented by other types of immittance values, which are not limited in the present disclosure.

Please refer to step S31. The heater 10 generates heat to increase the temperature of the reference sensing portion 30 and the temperature of the target sensing portion 40, and the gas under test is in contact with the above portions 30 and 40.

Please refer to step S32. When the temperatures of the reference sensing portion 30 and the target sensing portion 40 increase and the reference sensing portion 30 and the target sensing portion 40 are in contact with the gas under test, the controller 70 detects the immittance values of the reference sensing portion 30 and the target sensing portion 40, namely the measured reference resistance value $R_{ref}$ (measures reference immittance value) of the reference sensing portion 30 and the measured target resistance value $R_{sen}$ (measured target immittance value) of the target sensing portion 40. For example, the controller 70 detects the measured reference resistance value $R_{ref}$ of the first sensing layer 301 through the first conductive layer 303 and detects the measured target resistance value $R_{sen}$ of the second sensing layer 401 through the second conductive layer 403.

Please refer to step S33. The controller 70 calculates the reference coefficient of variation α according to the measured reference resistance value $R_{ref}$ and an initial reference resistance value $R_{ref0}$ (initial reference immittance value). The initial reference resistance value $R_{ref0}$ is associated with the reference sensing portion 30. For example, before the gas sensing device 100 is shipped, the target gas of the specified concentration, such as 0 ppm, is directed to be contact with the heated reference sensing portion 30. At this time, the controller 70 detects the resistance value (immittance value) of the reference sensing portion 30, and then this resistance value is served as the initial reference resistance value $R_{ref0}$, and is stored in a built-in storage element of the controller 70 or in a storage device. For example, the reference coefficient of variation α is a ratio of the measured reference resistance value $R_{ref}$ to the initial reference resistance value $R_{ref0}$ as shown in equation 1, or is a difference between the above two resistance values $R_{ref}$ and $R_{ref0}$. The reference coefficient of variation α is configured to reflect the degree of the affection of the current environmental variation, such as the unstable absorption of the oxygen, the variations in humidity or temperature, etc., to the reference sensing portion 30.

$$\alpha = R_{ref}/R_{ref0} \quad \text{(Equation 1)}$$

Please refer to step S34. The controller 70 calculates a target gas concentration value according to the reference coefficient of variation α, a correlation function F, the measured target resistance value $R_{sen}$, and a target gas concentration converting function. The correlation function F represents a correlation between the reference sensing portion 30 and the target sensing portion 40. For example, the correlation function F represents a dependency relationship between the measured reference resistance value $R_{ref}$ and the measured target resistance value $R_{sen}$. For another example, the correlation function F represents a dependency relationship between a variability of the measured reference resistance value $R_{ref}$ and a variability of the measured target resistance value $R_{sen}$. The target gas concentration converting function is configured to convert a calibration resistance value (calibration immittance value) to the target gas concentration value.

Figure 3B:
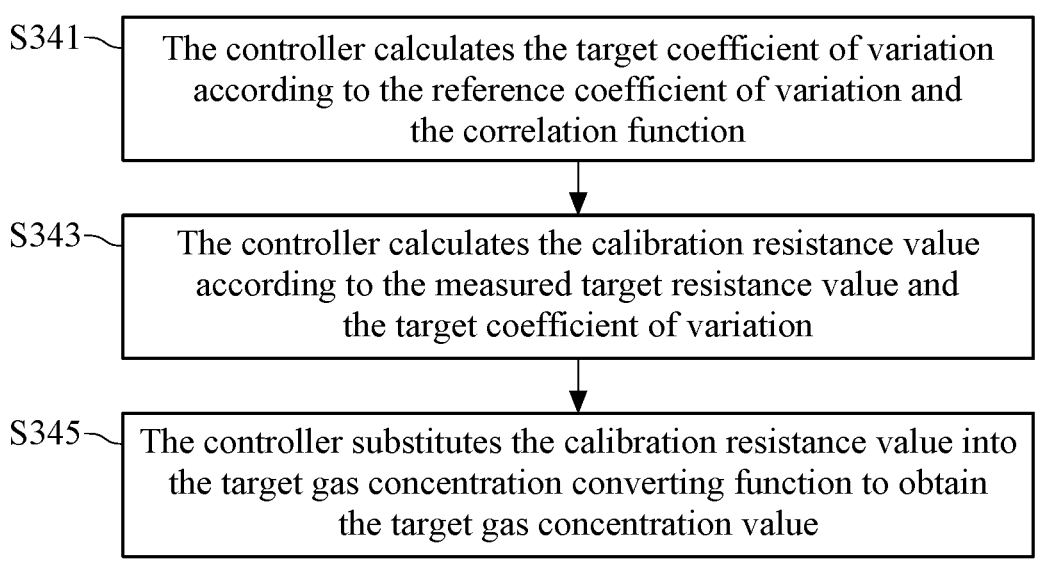
FIG. 3B is a detailed flowchart of step S34.

Please refer to FIG. 3B, which illustrates a detailed flowchart of step S34 of FIG. 3A. Please refer to step S341. The controller 70 calculates the target coefficient of variation β according to the reference coefficient of variation α and the correlation function F. For example, the controller 70 substitutes the reference coefficient of variation α into the correlation function F to obtain the target coefficient of variation β, as shown in equation 2.

$$\beta = F(\alpha) \quad \text{(Equation 2)}$$

Please refer to step S343. The controller 70 calculates the calibration resistance value $R_{cal}$ according to the measured target resistance value $R_{sen}$ and the target coefficient of variation β. For example, the controller 70 uses the quotient value of the measured target resistance value $R_{sen}$ divided by the target coefficient of variation β as the calibration resistance value $R_{cal}$ as shown in equation 3.

$$R_{cal} = R_{sen}/\beta \quad \text{(Equation 3)}$$

Please refer to step S345. The controller 70 substitutes the calibration resistance value $R_{cal}$ into the target gas concentration converting function to obtain the target gas concentration value.

Figure 4:
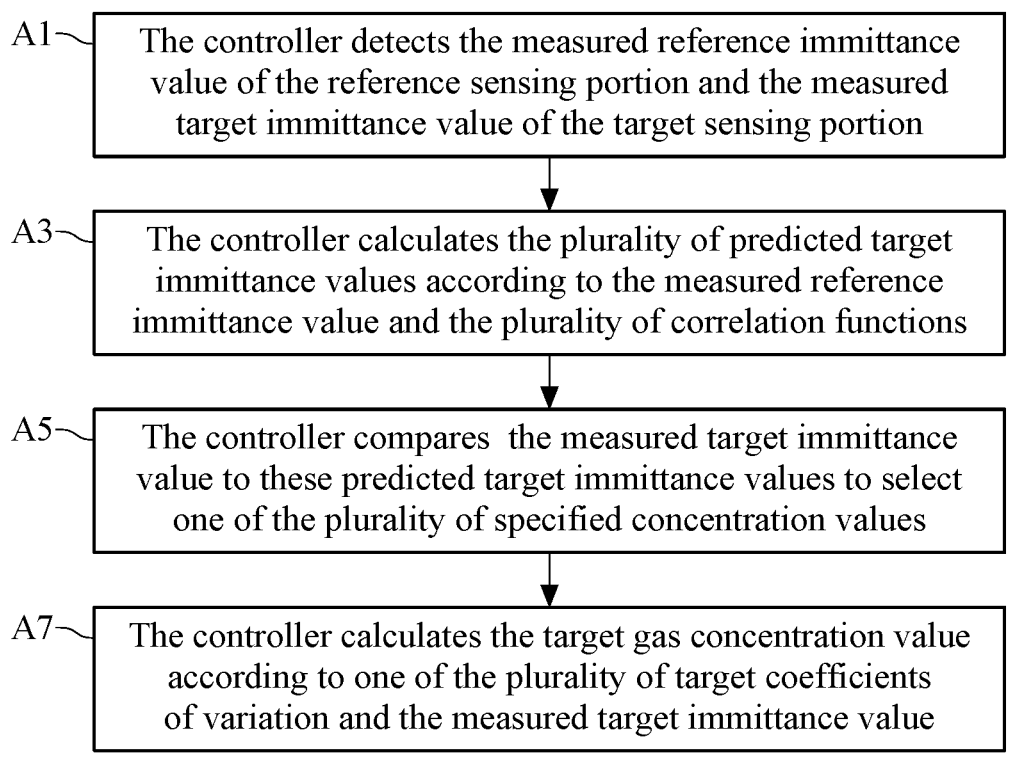
FIG. 4 is a flowchart of the gas concentration sensing method adapted to the first embodiment of the present disclosure.

Please refer to FIG. 4, which illustrates a flowchart of the gas concentration sensing method of the second example of the present disclosure. The gas concentration sensing method is adapted to the gas sensing device 100 capable of sensing the target gas as described in the first embodiment. Said gas sensing device 100 includes the heater 10, the reference sensing portion 30 low sensitive to the target gas, the target sensing portion 40 high sensitive to the target gas and the controller 70.

Please refer to FIG. 4. Basically, this example mainly includes an immittance obtaining stage A1, a range calculating stage A3, a range comparing stage A5, and a concentration calculating stage A7. In the immittance obtaining stage A1, the controller 70 may detect a measured reference immittance value of the reference sensing portion 30 and a measured target immittance value of the target sensing portion 40. In the range calculating stage A3, the controller 70 calculates a plurality of predicted target immittance values according to the measured reference immittance value and a plurality of correlation functions, wherein these correlation functions and these predicted target immittance values correspond to a plurality of specified concentration values. In the range comparing stage A5, the controller 70 compares the measured target immittance value to the plurality of predicted target immittance values for selecting one from these specified concentration values. In the concentration calculating stage A7, the controller 70 calculates a target gas concentration value according to one of the plurality of target coefficients of variation and the measured target immittance value.

Figure 5A:
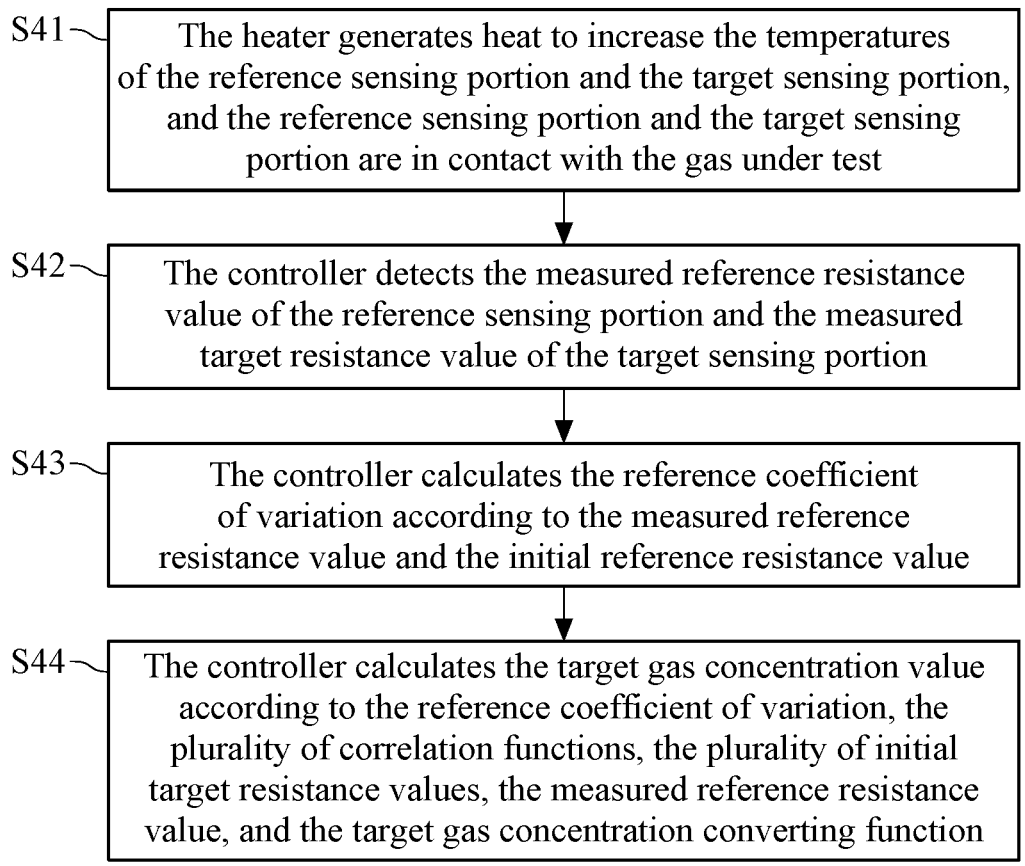
FIG. 5A is the flowchart of the gas concentration sensing method of the second example of the present disclosure.
Figure 5B:
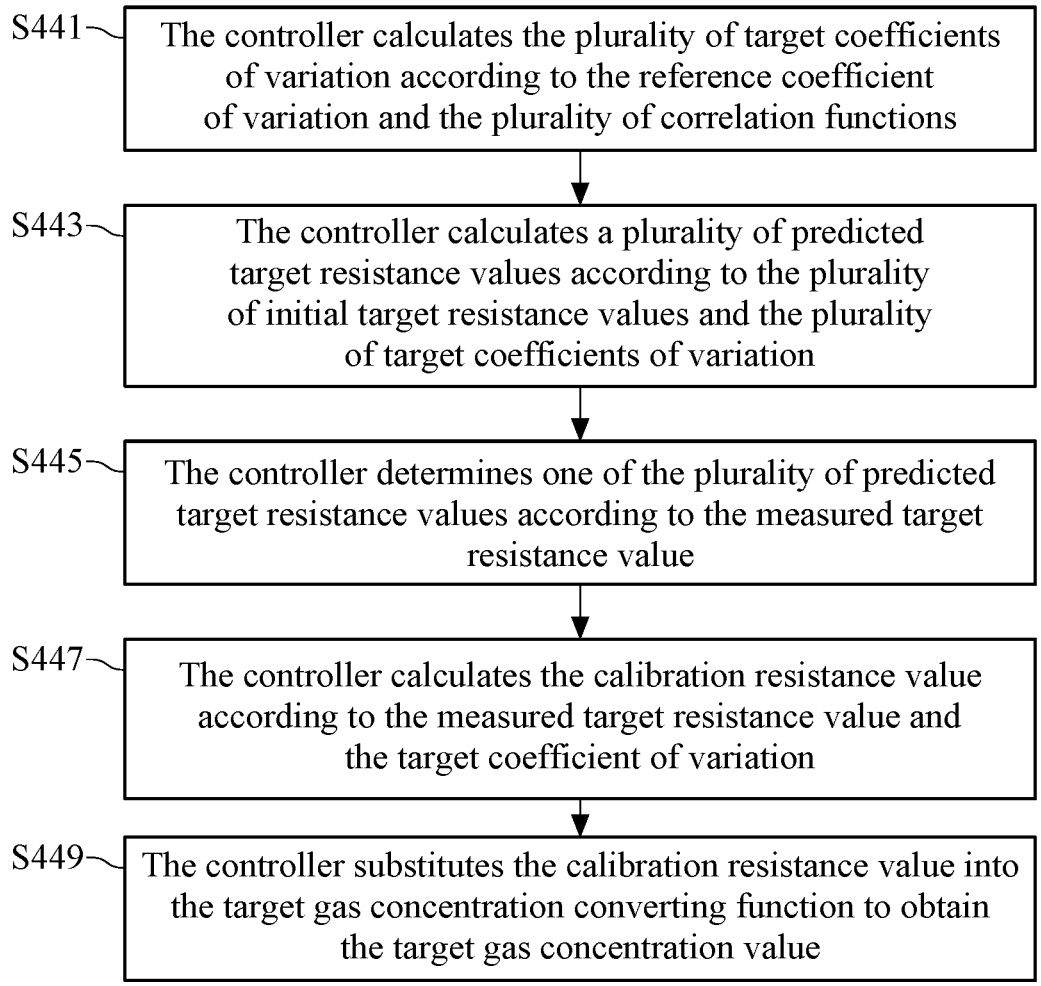
FIG. 5B is a detailed flowchart of step S44.

Please refer to FIG. 5A and FIG. 5B, which illustrate a flowchart and a detailed flowchart of the gas concentration sensing method of the second example of the present disclosure. Steps S41-S42 of FIG. 5A belong to the aforementioned immittance obtaining stage A1, steps S43, S441 and S443 belong to the aforementioned range calculating stage A3, step S445 belongs to the aforementioned range comparing stage A5, and steps S447 and S449 belong to the aforementioned concentration calculating stage A7.

Steps S41-S43 of FIG. 5A are basically identical to steps S31-S33 of FIG. 3. In short, the controller 70 detects the measured reference resistance value $R_{ref}$ (measures reference immittance value) of the reference sensing portion 30 and the measured target resistance value $R_{sen}$ (measured target immittance value) of the target sensing portion 40. The above two resistance values $R_{ref}$ and $R_{sen}$ are immittance values mentioned in the immittance obtaining stage A1, and the controller 70 calculates the reference coefficient of variation α according to the measured reference resistance value $R_{ref}$ and an initial reference resistance value $R_{ref0}$ (initial reference immittance value).

Please refer to step S44. The controller 70 calculates the target gas concentration value according to the reference coefficient of variation α, a plurality of correlation functions $F_{(k\ ppm)}$, a plurality of initial target resistance values $R_{sen\ 0,\ (k\ ppm)}$ (initial target immittance values), the measured target resistance value $R_{sen}$, and the target gas concentration converting function. The number of correlation functions $F_{(k\ ppm)}$ and the number of initial target resistance values $R_{sen\ 0,\ (k\ ppm)}$ both depend on the number of specified concentration values. For example, if the specified concentration values expressed in part per million (ppm) have four values, including 0 ppm, 20 ppm, 100 ppm and 200 ppm, the four corresponding correlation functions $F_{(k\ ppm)}$ are $F_{(0\ ppm)}$, $F_{(20\ ppm)}$, $F_{(100\ ppm)}$, and $F_{(200\ ppm)}$, and the four corresponding initial target resistance values $R_{sen\ 0,\ (k\ ppm)}$ are $R_{sen\ 0,\ (0\ ppm)}$, $R_{sen\ 0,\ (20\ ppm)}$, $R_{sen\ 0,\ (100\ ppm)}$, and $R_{sen\ 0,\ (200\ ppm)}$. Each of the plurality of correlation functions $F_{(k\ ppm)}$ represents a correlation between the reference sensing portion 30 and the target sensing portion 40 in contact with the target gas having one of the plurality of specified concentration values. For example, each of the correlation function $F_{(k\ ppm)}$ represents a dependency relationship between the measured reference resistance value $R_{ref}$ and the measured target resistance value $R_{sen}$ under each of the concentration values. For another example, the correlation function $F_{(k\ ppm)}$ represents a dependency relationship between a variability of the measured reference resistance value $R_{ref}$ and a variability of the measured target resistance value $R_{sen}$ under each of the concentration values. For example, before the gas sensing device 100 being shipped, the target gases of a plurality of specified concentration values, such as 0 ppm, 20 ppm, 100 ppm, and 200 ppm, are respectively directed to be in contact with the heated target sensing portion 40. At this time, the controller 70 detects the resistance values (or immittance values, such as $R_{sen\ 0,\ (0\ ppm)}$, $R_{sen\ 0,\ (20\ ppm)}$, $R_{sen\ 0,\ (100\ ppm)}$, and $R_{sen\ 0,\ (200\ ppm)}$) of the target sensing portion 40 under these specified concentration values, and then these resistance values are served as the plurality of initial target resistance values $R_{sen\ 0,\ (k\ ppm)}$, and are stored in a built-in storage element of the controller 70 or in a storage device.

Please refer to FIG. 5B, which illustrates a detailed flowchart of step S44 of FIG. 5A. Please refer to step S411. The controller 70 calculates a plurality of target coefficients of variation $\beta_{(k\ ppm)}$ according to the reference coefficient of variation $\alpha$ and a plurality of correlation functions $F_{(k\ ppm)}$. The number of target coefficients of variation $\beta_{(k\ ppm)}$ depends on the number of the specified concentration values. Following the previous example, the controller 70 substitutes the reference coefficient of variation $\alpha$ into four correlation functions $F_{(k\ ppm)}$ respectively to obtain four target coefficients of variation $\beta_{(k\ ppm)}$, including $\beta_{(0\ ppm)}$, $\beta_{(20\ ppm)}$, $\beta_{(100\ ppm)}$, and $\beta_{(200\ ppm)}$, as shown in equations 4-7 below.

$$\beta_{(0\ ppm)} = F_{(0\ ppm)}(\alpha) \quad \text{(Equation 4)}$$

$$\beta_{(20\ ppm)} = F_{(20\ ppm)}(\alpha) \quad \text{(Equation 5)}$$

$$\beta_{(100\ ppm)} = F_{(200\ ppm)}(\alpha) \quad \text{(Equation 6)}$$

$$\beta_{(100\ ppm)} = F_{(200\ ppm)}(\alpha) \quad \text{(Equation 7)}$$

Please refer to step S443. The controller 70 calculates a plurality of predicted target resistance values $R_{sen,\ pre,\ (k\ ppm)}$ (predicted target immittance values, namely the plurality of range reference values described in the range calculating stage A3) according to a plurality of initial target resistance values $R_{sen\ 0,\ (k\ ppm)}$ and a plurality of target coefficients of variation $\beta_{(k\ ppm)}$. Regarding the calculation approach of step S443, following the previous example, for each of the plurality of specified concentration values, such as 0 ppm, 20 ppm, 100 ppm, 200 ppm, the product of the initial target resistance value $R_{sen\ 0,\ (k\ ppm)}$ corresponding one of the plurality of specified concentration values and the target coefficient of variation $\beta_{(k\ ppm)}$ corresponding said one of the plurality of specified concentration values is served as the predicted target resistance value $R_{sen,\ pre,\ (k\ ppm)}$, including $R_{sen,\ pre,\ (0\ ppm)}$, $R_{sen,\ pre,\ (20\ ppm)}$, $R_{sen,\ pre,\ (100\ ppm)}$, and $R_{sen,\ pre,\ (200\ ppm)}$, as shown in equations 8-11 below.

$$R_{sen,pre,(0\ ppm)} = R_{sen\ 0,(0\ ppm)} * \beta_{(0\ ppm)} \quad \text{(Equation 8)}$$

$$R_{sen,pre,(20\ ppm)} = R_{sen\ 0,(20\ ppm)} * \beta_{(20\ ppm)} \quad \text{(Equation 9)}$$

$$R_{sen,pre,(100\ ppm)} = R_{sen\ 0,(100\ ppm)} * \beta_{(100\ ppm)} \quad \text{(Equation 10)}$$

$$R_{sen,pre,(200\ ppm)} = R_{sen\ 0,(200\ ppm)} * \beta_{(200\ ppm)} \quad \text{(Equation 11)}$$

Please refer to step S445. The controller 70 determines one of the plurality of predicted target resistance values $R_{sen,\ pre,\ (k\ ppm)}$ according to the measured target resistance value $R_{sen}$. For example, the controller 70 calculates a plurality of difference values between the measured target resistance value $R_{sen}$ and each of the plurality of predicted target resistance values $R_{sen,\ pre,\ (k\ ppm)}$, and selects the predicted target resistance values $R_{sen,pre,\ (x\ ppm)}$ corresponding to the minimum one of difference values (or the minimum one of the absolute difference values).

Please refer to step S447. The controller 70 calculates the calibration resistance value $R_{cal}$ (calibration immittance value) according to the measured target resistance value $R_{sen}$ and the target coefficient of variation $\beta_{(x\ ppm)}$, wherein the target coefficient of variation $\beta_{(x\ ppm)}$ is one of the plurality of target coefficients of variation $\beta_{(k\ ppm)}$, and the specified concentration value corresponding to the target coefficient of variation $\beta_{(x\ ppm)}$ equals to the specified concentration value corresponding to the predicted target resistance values $R_{sen,\ pre,\ (x\ ppm)}$. Regarding the calculation approach of the calibration resistance value $R_{cal}$, for example, the controller 70 uses the quotient value of the measured target resistance value $R_{sen}$ divided by the target coefficient of variation $\beta_{(x\ ppm)}$ as the calibration resistance value $R_{cal}$, as shown in equation 12.

$$R_{cal} = R_{sen}/\beta_{(x\ ppm)} \quad \text{(Equation 12)}$$

Please refer to step S449. The controller 70 substitutes the calibration resistance value $R_{cal}$ into the target gas concentration converting function to obtain the target gas concentration value.

Figure 6:
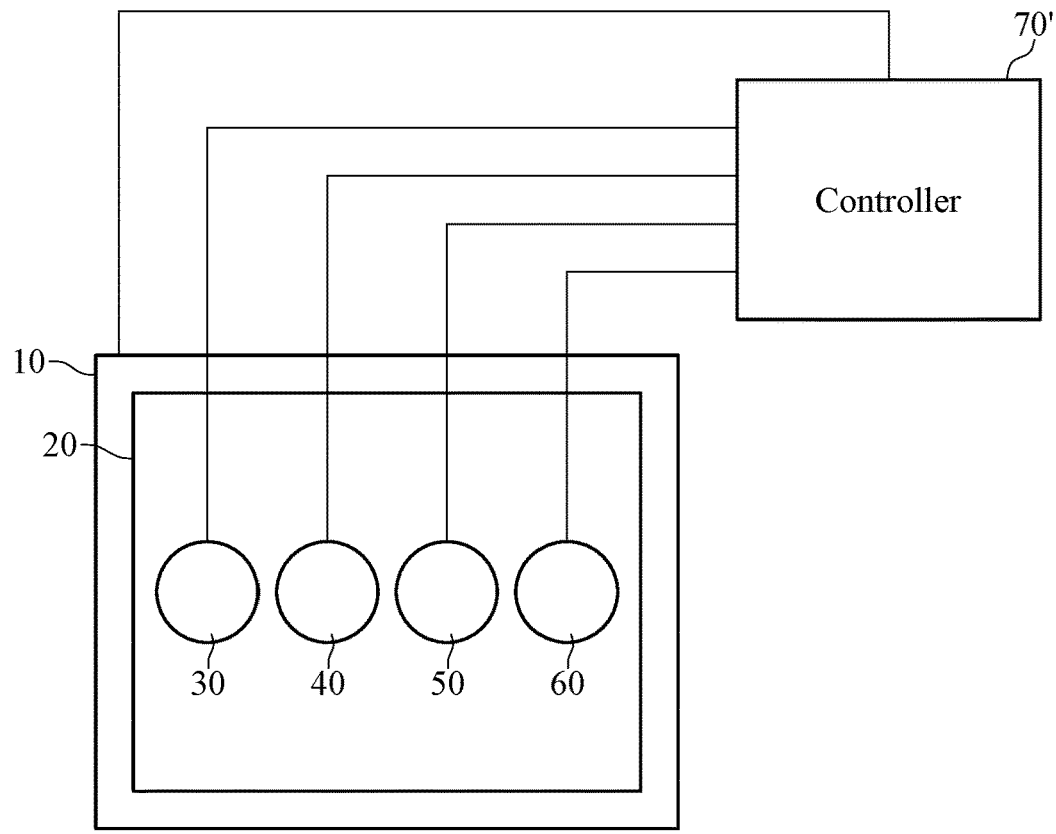
FIG. 6 is an architecture diagram of the gas sensing device of the second embodiment of the present disclosure.

Please refer to FIG. 6, which illustrates an architecture diagram of the gas sensing device 200 of the second embodiment of the present disclosure. The reference sensing portion 30 and the target sensing portion 40 of the gas sensing device 100 of the aforementioned first embodiment are respectively called a first reference sensing portion 30 and a first target sensing portion 40 in the second embodiment. The gas sensing device 200 of the second embodiment further includes a second reference sensing portion 50 and a second target sensing portion 60, and the controller 70' of the second embodiment further electrically connects to the second reference sensing portion 50 and the second target sensing portion 60. The second target sensing portion 60 is served as a backup sensing element of the first target sensing portion 40. Therefore, the example of the second target sensing portion 60 will not be repeated in the following description of the gas concentration sensing method adapted to the second embodiment of the gas sensing device 200.

Figure 7:
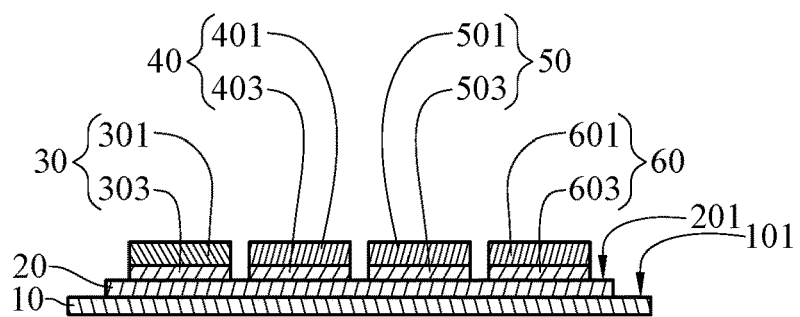
FIG. 7 is a side view of the heater, the dielectric layer, the first reference sensing portion, the first target sensing portion, the second reference sensing portion, the second target sensing portion.

Specifically, the gas sensing device 200 is capable of sensing a concentration of a target gas in a gas under test. The gas sensing device 200 includes a heater 10, a dielectric layer 20, a first reference sensing portion 30, a first target sensing portion 40, a second target sensing portion 60, and a controller 70'. Please refer to FIG. 7, which illustrates a side view of elements including the heater 10, the dielectric layer 20, the first reference sensing portion 30, the first target sensing portion 40, the second reference sensing portion 50, and the second target sensing portion 60.

For example, the heater 10 may receive the power from an external power source (not depicted) through the controller 70'. The heater 10 generates heat on its surface 101. For example, the heater 10 has a single heating element to heat the first reference sensing portion 30, the first target sensing portion 40, and the second reference sensing portion 50 together, and the second target sensing portion 60 is heated by the single heating element or is preferably heated by another heating element. For another example, the heater 10 has multiple heating elements to heat the first reference sensing portion 30, the first target sensing portion 40, the second reference sensing portion 50, and the second target sensing portion 60 respectively. The purpose of disposing the heater 10 is to heat the first reference sensing portion 30, the first target sensing portion 40, and the second reference sensing portion 50 to the same temperature at the same time, and the second target sensing portion 60 is preferably to be heated to the same temperature independently. The present disclosure does not limit the number of heating elements of the heater 10 as long as the purpose is achieved.

The dielectric layer 20 is disposed on the surface 101 of the heater 10. The dielectric layer 20 has a supporting side 201. The supporting side 201 preferably faces away from the surface 101 of the heater 10. The reference sensing portion 30, the target sensing portion 40, the second reference sensing portion 50 and the second target sensing portion 60 are disposed on the supporting side 201.

In the second embodiment, the first reference sensing portion 30 is identical to the reference sensing portion 30 of the first embodiment, and the first target sensing portion 40 is identical to the target sensing portion 40 of the first embodiment, so the description will not be repeated. In this embodiment, the measured reference immittance value and the measured target immittance value described in the first embodiment are called "first measured reference immittance value" and "first measured target immittance value".

The second reference sensing portion 50 includes a third sensing layer 501 and a third conductive layer 503. The third sensing layer 501 is a metal oxide, and is sensitive to the target gas. The third conductive layer 503 connects to the third sensing layer 501 so that the current transmitted by the third conductive layer 503 may flow through the third sensing layer 501. Therefore, the controller 70' may detect an immittance value of the third conductive layer 503, and this immittance value is called "second measured reference immittance value" hereafter. For the convenience of illustration, resistance values are preferred as examples of the immittance value in the following content. The second reference sensing portion 50 is configured to reflect the variation degree of the sensing material of the first target sensing portion 40 (namely the second sensing layer 401).

The second target sensing portion 60 includes a fourth sensing layer 601 and a fourth conductive layer 603. The fourth sensing layer 601 is a metal oxide, and is sensitive to the target gas. The fourth conductive layer 603 connects to the fourth sensing layer 601 so that the current transmitted by the fourth conductive layer 603 may flow through the fourth sensing layer 601. Therefore, the controller 70' may detect an immittance value of the fourth conductive layer 603, and this immittance value is called "second measured target immittance value" hereafter. For the convenience of illustration, resistance values are preferred as examples of the immittance value in the following content. The second target sensing portion 60 is served as a backup of the first target sensing portion 40. For example, when the controller 70' determines that the first target sensing portion 40 is abnormal, the controller 70' may change to detect the immittance value of the second target sensing portion 60 being in contact with the gas under test for calculating the concentration value of the target gas in the gas under test. For another example, the controller 70' detects the immittance value of the second target sensing portion 60 after the temperature of the second target sensing portion 60 heated by the heater 10 reaches to the temperatures of the first and second reference sensing portion 30, 50. In other embodiments, the arrangement of the second target sensing portion 60 may be neglected or may include a plurality of the second target sensing portion 60. The present disclosure does not limit the number of the second target sensing portion 60.

The sensitivity of the first reference sensing portion 30 to the target gas is lower than each of the sensitivities of the first target sensing portion 40, the second reference sensing portion 50, and the second target sensing portion 60 to the target gas. In order to achieve high or low sensitivity of the sensing material to the target gas, deposition with a specific metal may be adopted. For example, sensing materials, such as tungsten oxide ($WO_3$) and tin oxide ($SnO_2$), may be deposited in the supporting side 201 of the dielectric layer 20. The deposition methods is "drop coating" or "sputtering deposition". The portion of the supporting side 201 deposited with tungsten oxide may be served as the first sensing layer 301 of the first reference sensing portion 30, wherein the particle size of the sensing material is 30 nanometers and the thickness is 0.1 micrometers. The portions of the supporting side 201 deposited with tin oxide may be served as the second sensing layer 401 of the first target sensing portion 40, the third sensing layer 501 of the second reference sensing layer 50, and the fourth sensing layer 601 of the second target sensing portion 60, wherein the particle size of the sensing material in the second sensing layer 401 is 7-10 nanometers and the thickness is 1 micrometer, the particle size of the sensing material in the third sensing layer 501 is 7-10 nanometers and the thickness is 2.5 micrometers, and the particle size of the sensing material in the fourth sensing layer 601 is 7-10 nanometers and the thickness is 3 micrometers. The present disclosure does not limit the area and the kind of the deposited sensing material of the first sensing layer 301, the second sensing layer 401, the third sensing layer 501, and the fourth sensing layer 601, and the present disclosure does not limit the area and the thickness of the first conductive layer 303, the second conductive layer 403, the third conductive layer 503, and the fourth conductive layer 603. Regarding the sensitivities of the first target sensing portion 40, the second reference sensing portion 50, and the second target sensing portion 60 to the target gas, it is preferable that the differences from them to the sensitivity of the first reference sensing portion 30 to the target gas is large, and the best case of the first reference sensing portion 30 is non-sensitive. On the other hand, it is preferable that the sensitivities of the first target sensing portion 40, the second reference sensing portion 50, and the second target sensing portion 60 to the target gas are large.

Please refer to FIG. 6. The controller 70' electrically connects to the heater 10, the first reference sensing portion 30, the first target sensing portion 40, the second reference sensing portion 50, and the second target sensing portion 60. For example, the controller 70' further includes a heating driver (not depicted) configured to drive one or more heating elements of the heater 10. When the heater 10 heats the first reference sensing portion 30, the first target sensing portion 40, and the second reference sensing portion 50 (the second target sensing portion 60 may be heated at the same time) and the gas under test is directed to the gas sensing device 200, the controller 70' detects the first measured reference immittance value of the first reference sensing portion 30, the first measured target immittance value of the first target sensing portion 40, and the second measured reference value of the second reference sensing portion 50, while the second measured target immittance value of the second target sensing portion 60 may be included as well. In addition, the controller 70' is configured to obtain at least one of a plurality of default data. Therefore, the controller 70' may calculate the target gas concentration value in the gas under test according to the first measured reference immittance value, the first measured target immittance value, the second measured reference immittance value, (the second measured target immittance value) and the default data.

Regarding the storage of the default data, for example, a built-in storage element of the controller 70' may be adopted. For another example, a storage device outside the controller 70' may be adopted. This storage device communicably connects to the controller 70' so that the controller 70' may obtain the default data.

Said default data includes a plurality of initial reference resistance values (immittance values), a plurality of initial target resistance values (immittance values), a plurality of specified concentration values, a plurality of correlation functions, and at least one target gas concentration converting function. The specific contents of each of the default data will be described along with the examples of the gas concentration sensing method of the present disclosure.

Figure 8:
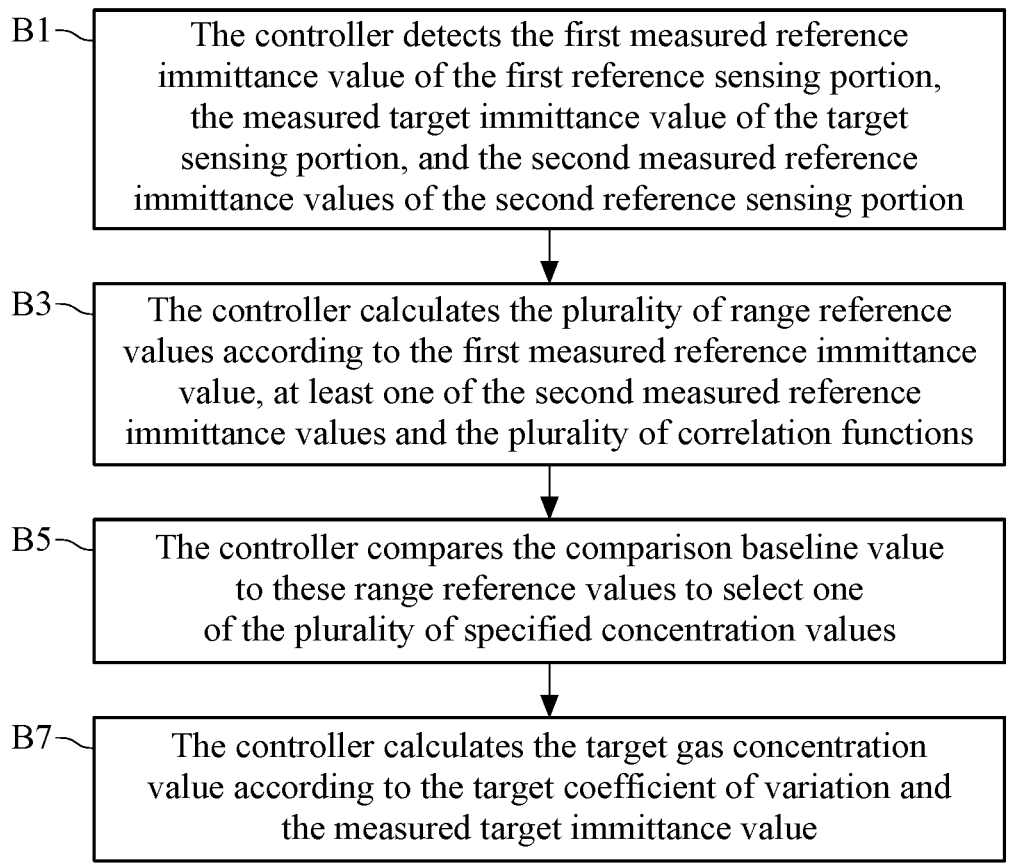
FIG. 8 is a flowchart of the gas concentration sensing method adapted to the second embodiment of the present disclosure.

Please refer to FIG. 8, which illustrates a flowchart of the gas concentration sensing method adapted to the second embodiment of the present disclosure. The gas concentration sensing method is adapted to the gas sensing device 200 capable of sensing the target gas as described in the second embodiment. Said gas sensing device 200 includes the heater 10, the first reference sensing portion 30 low sensitive to the target gas, the target sensing portion 40 (namely the first target sensing portion 40 as described previously) high sensitive to the target gas, the second reference sensing portion 50 high sensitive to the target gas and the controller 70'.

Please refer to FIG. 8. Four examples of the gas concentration sensing method adapted to the second embodiment of the gas sensing device are described below. Basically, similar to the second example of the aforementioned first embodiment, four examples described below mainly include an immittance obtaining stage B1, a range calculating stage B3, a range comparing stage B5, and concentration calculating stage B7 as shown in FIG. 8. In the immittance obtaining stage B1, when the first reference sensing portion 30 and the target sensing portion 40 are in contact with the gas under test, the controller 70' may detect a first measured reference immittance value of the first reference sensing portion 30, a first measured target immittance value of the target sensing portion 40, and the second measured reference immittance value of the second reference sensing portion 50. In the range calculating stage B3, the controller 70' calculates a plurality of range reference values according to the first measured reference immittance value, the second measured reference immittance values, and a plurality of correlation functions, with both the plurality of correlation functions and the plurality of range reference values corresponding to a plurality of specified concentration values. In the range comparing stage B5, the controller 70' compares the aforementioned plurality of range reference values to a comparison baseline value to further determine which range of the specified concentration value this comparison baseline value belongs to, namely to select one from the plurality of specified concentration values. In the concentration calculating stage B7, the controller 70' calculates a target gas concentration value according to a target coefficient of variation and the measured target immittance value, namely, calculating the concentration of the target gas in the gas under test, wherein the target coefficient of variation corresponds to said one of the plurality of specified concentration values.

Figure 9A:
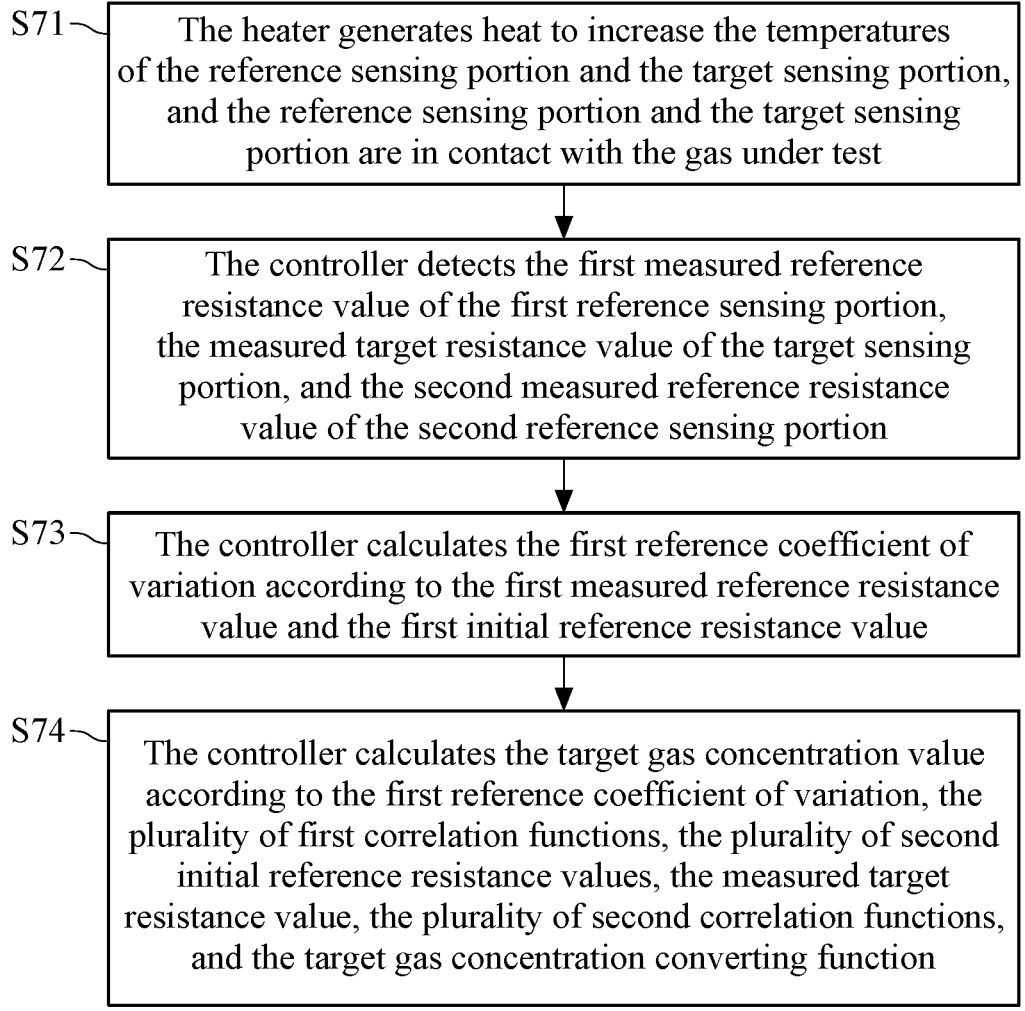
FIG. 9A is a flowchart of the gas concentration sensing method of the first example of the present disclosure.
Figure 9B:
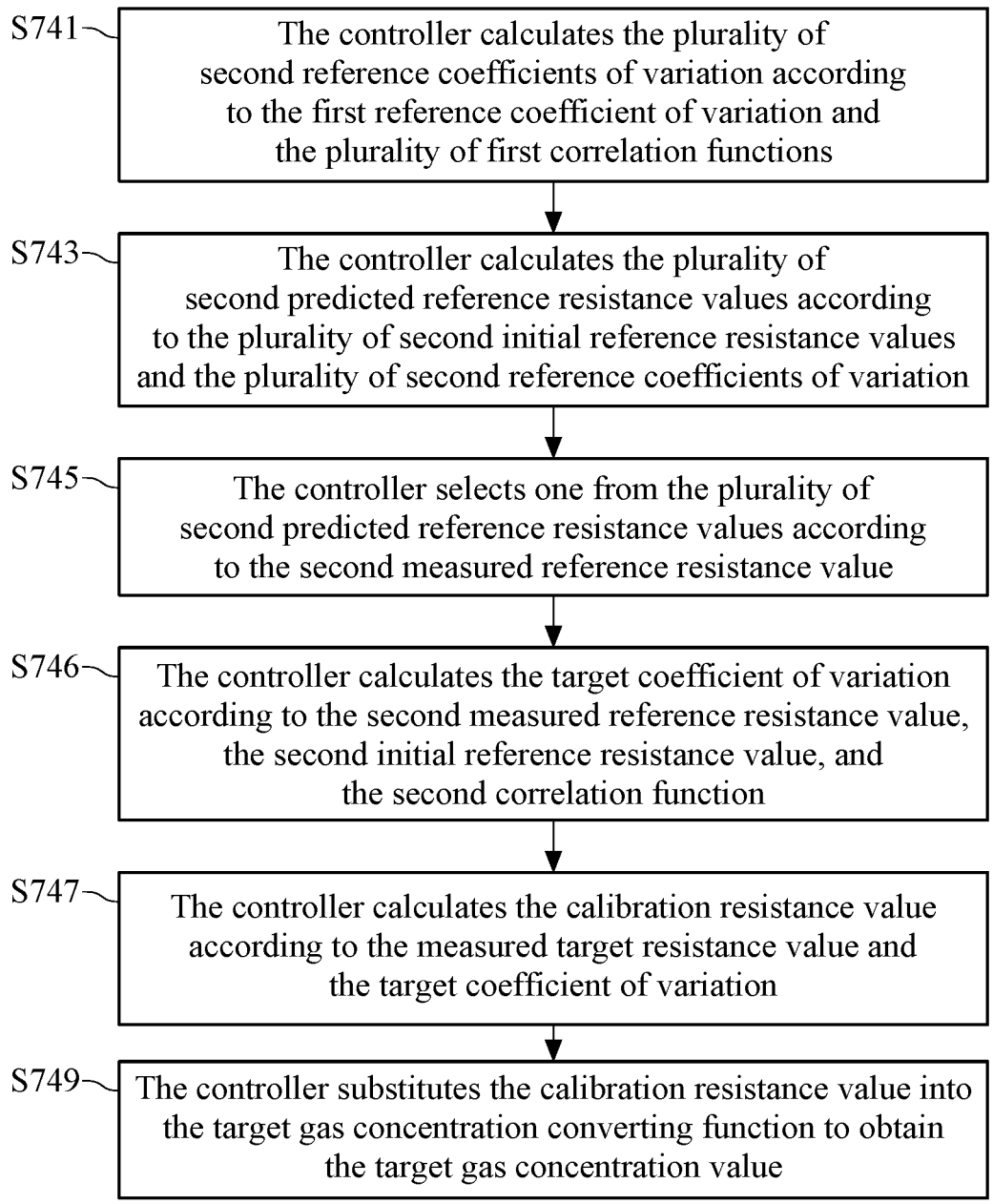
FIG. 9B is a detailed flowchart of step S74.

Please refer to FIGS. 9A and 9B, which illustrate a flowchart and a detailed flowchart of the gas concentration sensing method of the first example of the present disclosure. Steps S71-S73 of FIG. 9A belong to the aforementioned immittance obtaining stage B1, steps S73, S741 and S743 belong to the aforementioned range calculating stage B3, step S745 belongs to the aforementioned range comparing stage B5, and steps S747 and S749 belong to the concentration calculating stage B7.

Please refer to step S71. The heater 10 generates heat to increase the temperatures of the first reference sensing portion 30, the target sensing portion 40, and the second reference sensing portion 50, and the gas under test is in contact with the above portions 30, 40 and 50.

Please refer to step S72, when the temperatures of the first reference sensing portion 30, the target sensing portion 40, and the second reference sensing portion 50 increase and the above portions 30, 40 and 50 are in contact with the gas under test, the controller 70' detects the first measured reference resistance value $R_{ref1}$ (the first measured reference immittance value) of the first reference sensing portion 30, the measured target resistance value $R_{sen}$ (the measured target immittance value) of the target sensing portion 40, and the second measured reference resistance value $R_{ref2}$ (the second measured reference immittance value) of the second reference sensing portion 50. In short, the first measured reference resistance value $R_{ref1}$, the measured target resistance value $R_{sen}$, and the second measured reference resistance value $R_{ref2}$ are immittance values as described in the immittance obtaining stage B1. For example, the controller 70' may detect the first measured reference resistance value $R_{ref1}$ of the first sensing layer 301 through the first conductive layer 303, detect the measured target resistance value $R_{sen}$ of the second sensing layer 401 through the second conductive layer 403, and detect the second measured reference resistance value $R_{ref2}$ of the third sensing layer 501 through the third conductive layer 503.

Please refer to step S73. The controller 70' calculates the first reference coefficient of variation α according to the first measured reference resistance value $R_{ref1}$ and the first initial reference resistance value $R_{ref1, 0}$ (the first initial reference immittance value). The first initial reference resistance value $R_{ref1, 0}$ is associated with the first reference sensing portion 30. For example, before the gas sensing device 200 is shipped, the target gas of specified concentration such as 0 ppm is directed to be contact with the heated first reference sensing portion 30. At this time, the controller 70' detects the resistance value of the first reference sensing portion 30, and then this resistance value is served as the first initial reference resistance value $R_{ref1, 0}$ and is stored in a built-in storage element of the controller 70' or in a storage device. For example, the first reference coefficient of variation α is a ratio of the first measured reference resistance value $R_{ref1}$ to the first initial reference resistance value $R_{ref1, 0}$ as shown in equation 13. The first reference coefficient of variation α is configured to reflect the degree of the affection of the current environmental variation, such as the unstable absorption of the oxygen, the variation of the humidity, to the first reference sensing portion 30.

$$\alpha = R_{ref1}/R_{ref1,0} \qquad \text{(Equation 13)}$$

Please refer to step S74. The controller 70' calculates the target gas concentration value according to the first reference coefficient of variation α, a plurality of first correlation functions $F_{1(k\ ppm)}$, a plurality of second initial reference resistance values $R_{ref2, 0, (k\ ppm)}$ (second initial reference immittance values), the measured target resistance value $R_{sen}$, the second measured reference resistance value $R_{ref2}$ (the second measured reference immittance value), a plurality of second correlations $F_{2(k\ ppm)}$, and the target gas concentration converting function.

The number of the plurality of first correlation functions $F_{1(k\ ppm)}$, the number of the plurality of second initial reference resistance values $R_{ref2, 0, (k\ ppm)}$, and the number of the plurality of second correlations $F_{2(k\ ppm)}$ depend on the number of specified concentration values. For example, if the specified concentration values have four values including 0 ppm, 20 ppm, 100 ppm and 200 ppm, the four corresponding first correlation functions $F_{1\ (k\ ppm)}$ are $F_{1\ (0\ ppm)}$, $F_{1\ (20\ ppm)}$, $F_{1\ (100\ ppm)}$, and $F_{1\ (200\ ppm)}$, the four corresponding second initial reference resistance values $R_{ref2,\ 0,\ (k\ ppm)}$ are $R_{ref2,\ 0,\ (0\ ppm)}$, $R_{ref2,\ 0,\ (20\ ppm)}$, $R_{ref2,\ 0,\ (100\ ppm)}$, and $R_{ref2,\ 0,\ (200\ ppm)}$, and the four corresponding second correlation functions $F_{2(k\ ppm)}$ are $F_{2\ (0\ ppm)}$, $F_{2\ (20\ ppm)}$, $F_{2\ (100\ ppm)}$, and $F_{2\ (200\ ppm)}$. Based on the condition of the target gas of every specified concentration values, each of the plurality of first correlation functions $F_{1\ (k\ ppm)}$ represents a correlation between the first reference sensing portion 30 and the second reference sensing portion 50. For example, the first correlation function $F_{1\ (k\ ppm)}$ represents a dependency relationship between the first measured reference resistance value $R_{ref1}$ and the second measured reference resistance value $R_{ref2}$. For another example, the first correlation function $F_{1\ (k\ ppm)}$ represents a dependency relationship between a variability of the first measured reference resistance value $R_{ref1}$ and a variability of the second measured reference resistance value $R_{ref2}$. Regarding the plurality of second initial reference resistance values $R_{ref2,\ 0,\ (k\ ppm)}$, for example, before the gas sensing device 200 is shipped, the target gases of a plurality of specified concentration values, such as 0 ppm, 20 ppm, 100 ppm, and 200 ppm, are directed to be in contact with the heated second reference sensing portion 50 respectively. At this time, the controller 70' detects the resistance values of the second reference sensing portion 50, such as $R_{ref2,\ 0,\ (0\ ppm)}$, $R_{ref2,\ 0,\ (20\ ppm)}$, $R_{ref2,\ 0,\ (100\ ppm)}$, and $R_{ref2,\ 0,\ (200\ ppm)}$, and then these resistance values are served as the plurality of second initial reference resistance value $R_{ref2,\ 0,\ (k\ ppm)}$ and are stored in a built-in storage element of the controller 70' or in a storage device. Based on the condition of the target gas of every specified concentration values, each of the plurality of second correlation functions $F_{2(k\ ppm)}$ represents a dependency relationship between the second reference sensing portion 50 and the target sensing portion 40. For example, the second correlation functions $F_{2(k\ ppm)}$ represent a dependency relationship between the second measured reference resistance $R_{ref2}$ and the measured target resistance value $R_{sen}$. For another example, the second correlation functions $F_{2(k\ ppm)}$ represent a dependency relationship between a variability of the second measured reference resistance $R_{ref2}$ and a variability of the measured target resistance value $R_{sen}$.

Please refer to FIG. 9B, which illustrates a detailed flowchart of step S74 of FIG. 9A. Steps 741 and S743 belong to the range calculating stage B3, step S744 belongs to the range comparing stage B5, and steps S746, S747, and S749 belong to the concentration calculating stage B7.

Please refer to step S741. The controller 70' calculates the plurality of second reference coefficients of variation $\gamma_{(k\ ppm)}$ according to the first reference coefficient of variation α and the plurality of first correlation functions $F_{1\ (k\ ppm)}$. The number of the second reference coefficients of variation $\gamma_{(k\ ppm)}$ depends on the number of the plurality of first correlation functions $F_{1\ (k\ ppm)}$. Following the previous example, the controller 70' substitutes the first reference coefficient of variation α into four first correlation functions $F_{1\ (k\ ppm)}$ respectively to obtain four second reference coefficients of variation $\gamma_{(k\ ppm)}$, including $\gamma_{(0\ ppm)}$, $\gamma_{(20\ ppm)}$, $\gamma_{(100\ ppm)}$, and $\gamma_{(200\ ppm)}$, as shown in equations 14-17 below.

$$\gamma_{(0\ ppm)} = F_{1(0\ ppm)}(\alpha) \qquad \text{(Equation 14)}$$

$$\gamma_{(20\ ppm)} = F_{1(20\ ppm)}(\alpha) \qquad \text{(Equation 15)}$$

$$\gamma_{(100\ ppm)} = F_{1(200\ ppm)}(\alpha) \qquad \text{(Equation 16)}$$

$$\gamma_{(100\ ppm)} = F_{1(200\ ppm)}(\alpha) \qquad \text{(Equation 17)}$$

Please refer to step S743. The controller 70' calculates a plurality of second predicted reference resistance values $R_{ref2,\ pre,\ (k\ ppm)}$ (second predicted reference immittance values, which are the plurality of range reference values as described in the range calculating stage B3) according to a plurality of second initial reference resistance values $R_{ref2,\ 0,\ (k\ ppm)}$ and the plurality of second reference coefficients of variation $\gamma_{(k\ ppm)}$. Regarding the calculation approach of step S743, following the previous example, for each of the plurality of specified concentration values, such as 0 ppm, 20 ppm, 100 ppm, and 200 ppm, the product of the second initial reference resistance values $R_{ref2,\ 0,\ (k\ ppm)}$ corresponding one of the plurality of specified concentration values and the second reference coefficients of variation $\gamma_{(k\ ppm)}$ corresponding said one of the plurality of specified concentration values is served as the second predicted reference resistance values $R_{ref2,\ pre,\ (k\ ppm)}$, including $R_{ref2,\ pre,\ (0\ ppm)}$, $R_{ref2,\ pre,\ (20\ ppm)}$, $R_{ref2,\ pre,\ (100\ ppm)}$, and $R_{ref2,\ pre,\ (200\ ppm)}$, as shown in equations 18-21 below.

$$R_{ref2,pre,(0\ ppm)} = R_{ref2,0,(0\ ppm)} * \gamma_{(0\ ppm)} \qquad \text{(Equation 18)}$$

$$R_{ref2,pre,(20\ ppm)} = R_{ref2,0,(20\ ppm)} * \gamma_{(20\ ppm)} \qquad \text{(Equation 19)}$$

$$R_{ref2,pre,(100\ ppm)} = R_{ref2,0,(100\ ppm)} * \gamma_{(100\ ppm)} \qquad \text{(Equation 20)}$$

$$R_{ref2,pre,(200\ ppm)} = R_{ref2,0,(200\ ppm)} * \gamma_{(200\ ppm)} \qquad \text{(Equation 21)}$$

Please refer to step S745. The controller 70' selects one from the plurality of second predicted reference resistance values $R_{ref2,\ pre,\ (k\ ppm)}$ according to the second measured reference resistance values $R_{ref2}$ (namely the comparison baseline value as described in the range comparing stage B5). For example, the controller 70' calculates a plurality of difference values between the second measured reference resistance values $R_{ref2}$ and each of the plurality of second predicted reference resistance values $R_{ref2,\ pre,\ (k\ ppm)}$ and selects the second predicted reference resistance value $R_{ref2,\ pre,\ (x\ ppm)}$ corresponding to the minimum one of difference values (or the minimum one of the absolute difference values).

Please refer to step S746. The controller 70' calculates the target coefficient of variation $\beta_{(x\ ppm)}$ according to the second measured reference resistance value $R_{ref2}$, the second initial reference resistance values $R_{ref2,\ 0,\ (x\ ppm)}$, and the second correlation functions $F_{2\ (x\ ppm)}$. The second initial reference resistance values $R_{ref2,\ 0,\ (x\ ppm)}$, the second predicted reference resistance values $R_{ref2,\ 0,\ (x\ ppm)}$ selected in step S745, and the second correlation functions $F_{2\ (x\ ppm)}$ correspond to the same concentration value x. In other words, this target coefficient of variation $\beta_{(x\ ppm)}$ is served as a parameter in the concentration calculating stage B7. Regarding the calculation approach of the target coefficient of variation $\beta_{(x\ ppm)}$, for example, the controller 70' uses value obtained based on the second correlation function $F_{2\ (x\ ppm)}$ using the quotient value of the second measured reference resistance value $R_{ref2}$ divided by the second initial reference resistance values $R_{ref2,\ 0,\ (x\ ppm)}$ as input, as shown in equation 22, wherein the quotient value is the target coefficient of variation $\beta_{(x\ ppm)}$.

$$\beta_{(x\ ppm)} = F_{2(x\ ppm)}(R_{ref2}/R_{ref2,0,(x\ ppm)}) \qquad \text{(Equation 22)}$$

Please refer to step S747. The controller 70' calculates the calibration resistance value $R_{cal}$ (calibration immittance value) according to the measured target resistance value $R_{sen}$ and the target coefficient of variation $\beta_{(x\ ppm)}$. Regarding the calculation approach of the calibration resistance value $R_{cal}$, for example, the controller 70' uses the quotient value of measured target resistance value $R_{sen}$ divided by the target coefficient of variation $\beta_{(x\ ppm)}$ as the calibration resistance value $R_{cal}$, as shown in equation 23.

$$R_{cal}=R_{sen}/\beta_{(x\ ppm)} \qquad \text{(Equation 23)}$$

Please refer to step S749, the controller 70' substitutes the calibration resistance value $R_{cal}$ into the target gas concentration converting function to obtain the target gas concentration value.

Figure 10A:
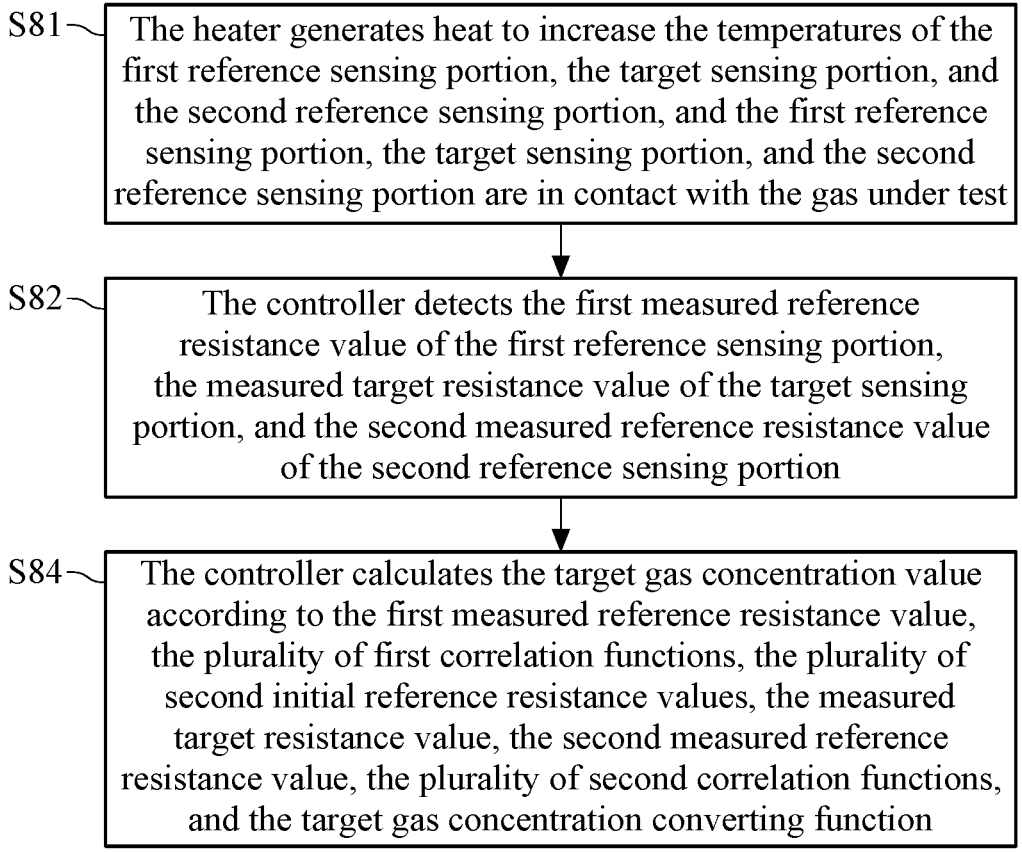
FIG. 10A is a flowchart of the gas concentration sensing method of the second example of the present disclosure.
Figure 10B:
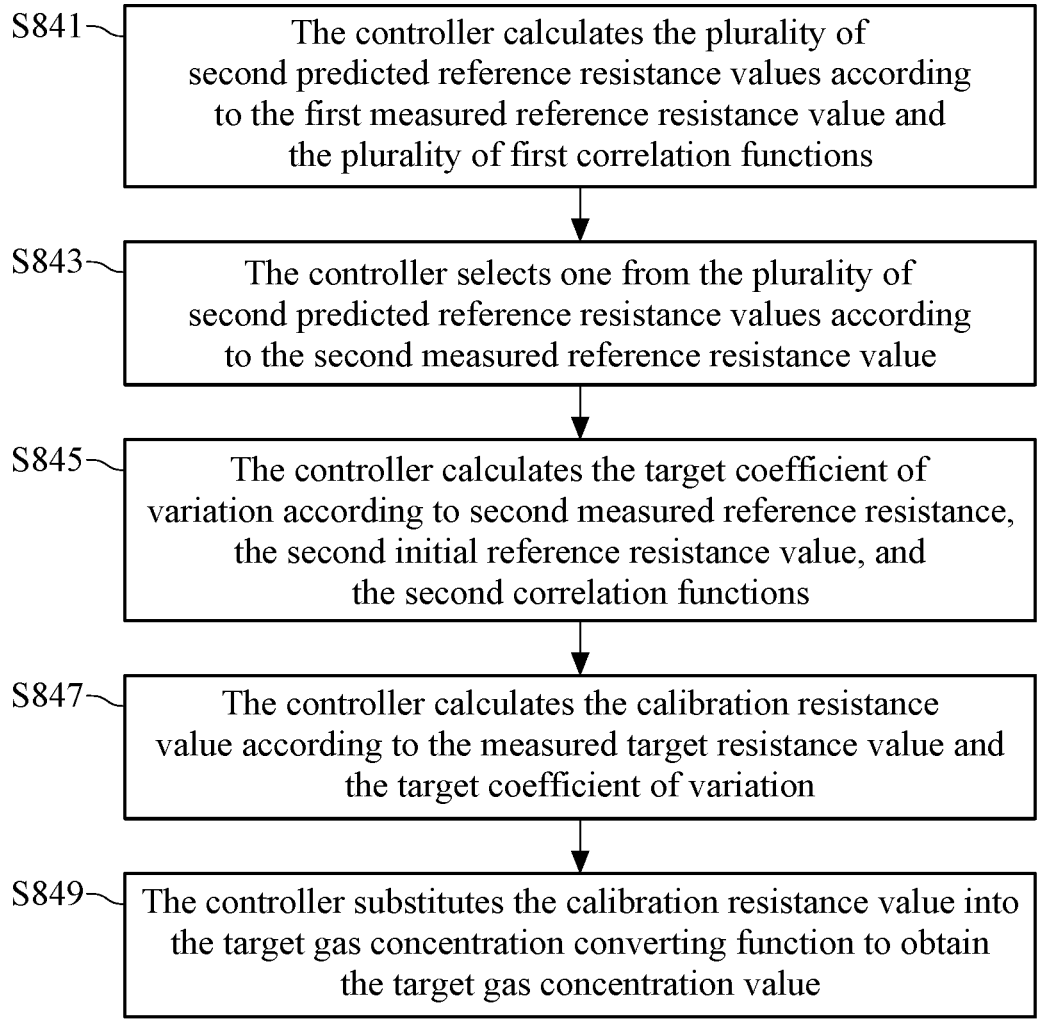
FIG. 10B is a detailed flowchart of step S84.

Please refer to FIGS. 10A and 10B, which illustrate a flowchart and a detailed flowchart of the gas concentration sensing method of the second example of the present disclosure. Steps S81-S82 of FIG. 10A belong to the aforementioned immittance obtaining stage B1, steps S841-S843 belong to the aforementioned range calculating stage B3, step S845 belongs to the aforementioned range comparing stage B5, and step S847 belongs to the aforementioned concentration calculating stage B7.

Steps S81-S82 of FIG. 10A are basically identical to steps S71-S72 of FIG. 9A. In short, the controller 70' detects the first measured reference resistance value $R_{ref1}$ (the first measured reference immittance value) of the first reference sensing portion 30, the measured target resistance value $R_{sen}$ (the measured target immittance value) of the target sensing portion 40, and the second measured reference resistance value $R_{ref2}$ (the second measured reference immittance value) of the second reference sensing portion 50.

Please refer to step S84. The controller 70' calculates the target gas concentration value according to the first measured reference resistance value $R_{ref1}$, a plurality of first correlation functions $F_{1(k\ ppm)}$, a plurality of second initial reference resistance values $R_{ref2,\ 0,\ (k\ ppm)}$ (second initial reference immittance values), the measured target resistance value $R_{sen}$, the second measured target resistance value $R_{ref2}$, a plurality of second correlations $F_{2(k\ ppm)}$, and the target gas concentration converting function.

Please refer to FIG. 10B, which illustrates a detailed flowchart of step S84 of FIG. 10A. Please refer to step S841. The controller 70' calculates a plurality of second predicted reference resistance values $R_{ref2,\ pre,\ (k\ ppm)}$ (second predicted reference immittance values, which is the plurality of range reference values as described in the range calculating stage B3) according to the first measured reference resistance value $R_{ref1}$ and a plurality of first correlation functions $F_{1\ (k\ ppm)}$. The number of the first correlation functions $F_{1\ (k\ ppm)}$ depends on the number of specified concentration values. For example, if the specified concentration values have four values, including 0 ppm, 20 ppm, 100 ppm and 200 ppm, the four corresponding first correlation functions $F_{1\ (k\ ppm)}$ are $F_{1\ (0\ ppm)}$, $F_{1\ (20\ ppm)}$, $F_{1\ (100\ ppm)}$, and $F_{1\ (200\ ppm)}$. Each of the plurality of first correlation functions $F_{1\ (k\ ppm)}$ represents a correlation between the first reference sensing portion 30 and the second reference sensing portion 50. For example, the first correlation function $F_{1\ (k\ ppm)}$ represents a dependency relationship between the first measured reference resistance value $R_{ref1}$ and the second measured reference resistance value $R_{ref2}$. Regarding the calculation approach of step S841, following the previous example, the controller 70' substitutes the first measured reference resistance value $R_{ref1}$ into four first correlation functions $F_{1\ (k\ ppm)}$ respectively to obtain four second predicted reference resistance values $R_{ref2,\ pre,\ (k\ ppm)}$, including $R_{ref2,\ pre,\ (0\ ppm)}$, $R_{ref2,\ pre,\ (20\ ppm)}$, $R_{ref2,\ pre,\ (100\ ppm)}$, and $R_{ref2,\ pre,\ (200\ ppm)}$, as shown in equations 24-27 below.

$$R_{ref2,pre,(0\ ppm)}=F_{1(0\ ppm)}(R_{ref1}) \qquad \text{(Equation 24)}$$

$$R_{ref2,pre,(20\ ppm)}=F_{1(20\ ppm)}(R_{ref1}) \qquad \text{(Equation 25)}$$

$$R_{ref2,pre,(100\ ppm)}=F_{1(100\ ppm)}(R_{ref1}) \qquad \text{(Equation 26)}$$

$$R_{ref2,pre,(200\ ppm)}=F_{1(200\ ppm)}(R_{ref1}) \qquad \text{(Equation 27)}$$

Please refer to step S843. The controller 70' selects one from the plurality of second predicted reference resistance values $R_{ref2,\ pre,\ (k\ ppm)}$ according to the second measured reference resistance values $R_{ref2}$ (namely the comparison baseline value as described in the range comparing stage B5). For example, the controller 70' calculates a plurality of difference values between the second measured reference resistance values $R_{ref2}$ and each of the plurality of second predicted reference resistance values $R_{ref2,\ pre,\ (k\ ppm)}$ and selects the second predicted reference resistance value $R_{ref2,\ pre,\ (x\ ppm)}$ corresponding to the minimum one of difference values (or the minimum one of the absolute difference values).

Please refer to step S845. The controller 70' calculates the target coefficient of variation $\beta_{(x\ ppm)}$ according to the second measured reference resistance value $R_{ref2}$, the second initial reference resistance values $R_{ref2,\ 0,\ (x\ ppm)}$, and the second correlation functions $F_{2\ (x\ ppm)}$. The second initial reference resistance values $R_{ref2,\ 0,\ (x\ ppm)}$, the second predicted reference resistance values $R_{ref2,\ 0,\ (x\ ppm)}$ selected in step S745, and the second correlation functions $F_{2\ (x\ ppm)}$ correspond to the same concentration value x. In other words, this target coefficient of variation $\beta_{(x\ ppm)}$ is served as a parameter in the concentration calculating stage B7. Regarding the calculation approach of the target coefficient of variation $\beta_{(x\ ppm)}$, for example, the controller 70' uses value obtained based on the second correlation function $F_{2\ (x\ ppm)}$ using the quotient value of the second measured reference resistance value $R_{ref2}$ divided by the second initial reference resistance values $R_{ref2,\ 0,\ (x\ ppm)}$ as input, as shown in equation 28, wherein the quotient value is the target coefficient of variation $\beta_{(x\ ppm)}$.

$$\beta_{(x\ ppm)}=F_{2(x\ ppm)}(R_{ref2}/R_{ref2,0,(x\ ppm)}) \qquad \text{(Equation 28)}$$

Please refer to step S847. The controller 70' calculates the calibration resistance value $R_{cal}$ (calibration immittance value) according to the measured target resistance value $R_{sen}$ and the target coefficient of variation $\beta_{(x\ ppm)}$. Regarding the calculation approach of the calibration resistance value $R_{cal}$, for example, the controller 70' uses the quotient value of measured target resistance value $R_{sen}$ divided by the target coefficient of variation $\beta_{(x\ ppm)}$ as the calibration resistance value $R_{cal}$, as shown in equation 29.

$$R_{cal}=R_{sen}/\beta_{(x\ ppm)} \qquad \text{(Equation 29)}$$

Please refer to step S849, the controller 70' substitutes the calibration resistance value $R_{cal}$ into the target gas concentration converting function to obtain the target gas concentration value.

Figure 11A:
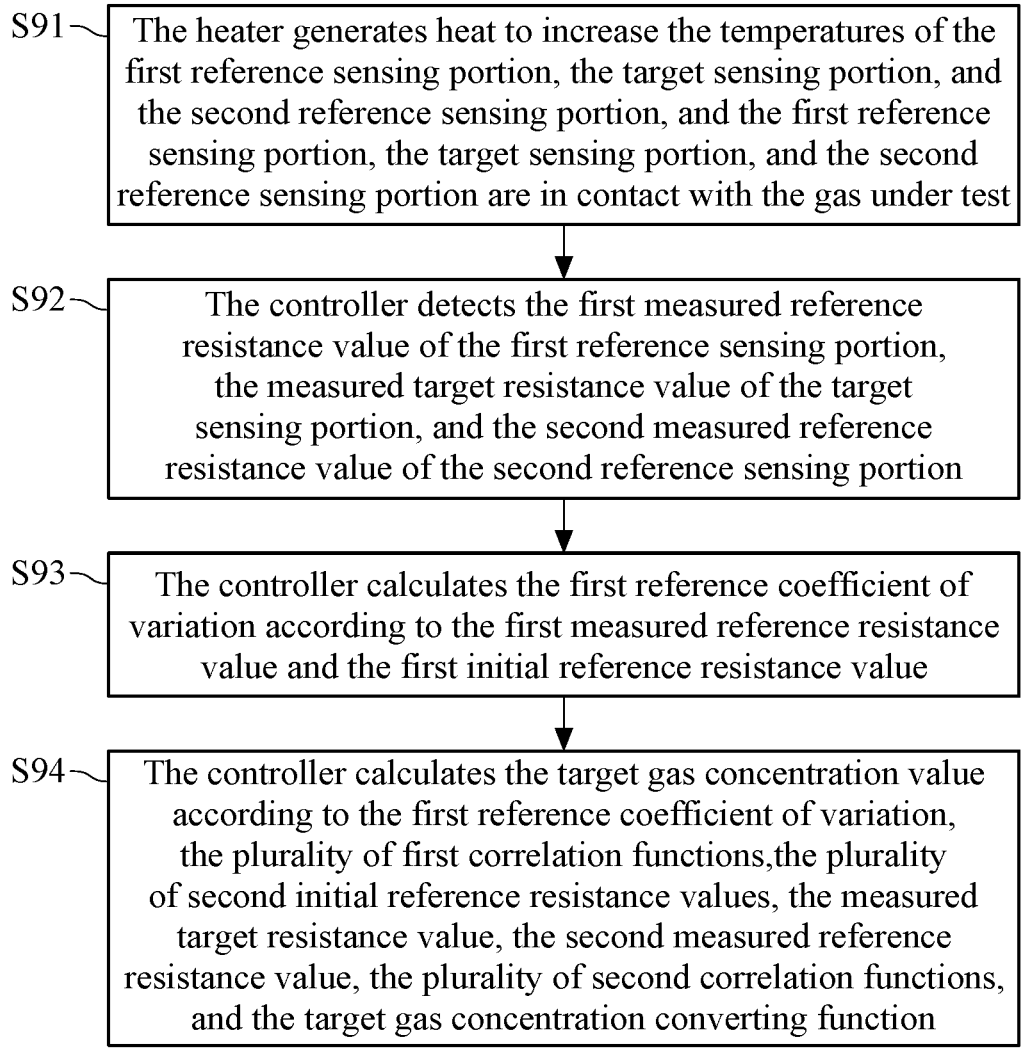
FIG. 11A is a flowchart of the gas concentration sensing method of the third example of the present disclosure.
Figure 11B:
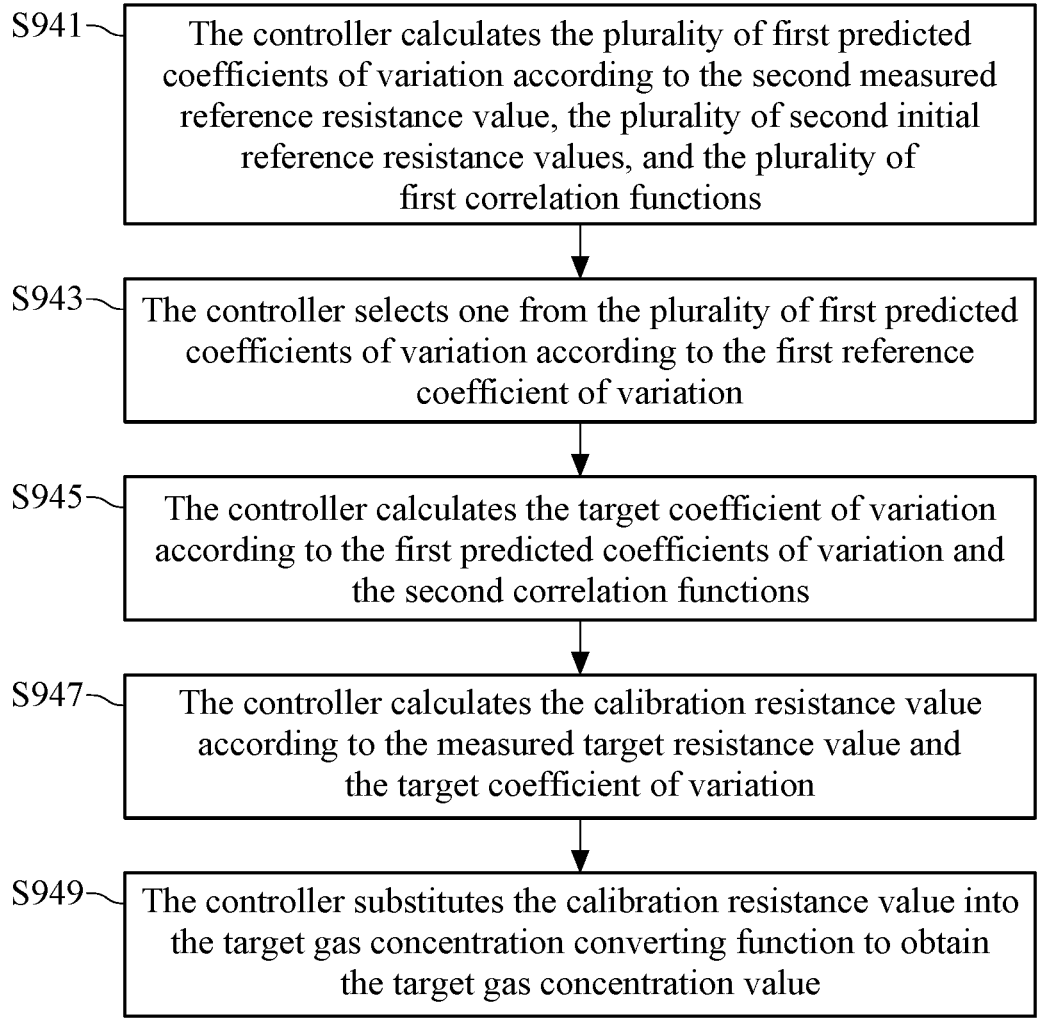
FIG. 11B is a detailed flowchart of step S94.

Please refer to FIGS. 11A and 11B, which illustrate a flowchart and a detailed flowchart of the gas concentration sensing method of the third example of the present disclosure. Steps S91-S92 of FIG. 11A belong to the aforementioned immittance obtaining stage B1, steps S93 and S941 belong to the aforementioned range calculating stage B3, step S943 belongs to the aforementioned range comparing stage B5 of FIG. 8, and step S945, S947, and S949 belong to the concentration calculating stage B7 of FIG. 8.

Steps S91-S93 of FIG. 11A are basically identical to steps S71-S73 of FIG. 9A. In short, the controller 70' detects the first measured reference resistance value $R_{ref1}$ (the first measured reference immittance value) of the first reference sensing portion 30, the measured target resistance value $R_{sen}$ (the measured target immittance value) of the target sensing portion 40, and the second measured reference resistance value $R_{ref2}$ (the second measured reference immittance value) of the second reference sensing portion 50. The controller 70' calculates the first reference coefficient of variation α according to the first measured reference resistance value $R_{ref1}$ and the first initial reference resistance value $R_{ref1, 0}$.

Please refer to step S94. The controller 70' calculates the target gas concentration value according to the first reference coefficient of variation α, a plurality of second initial reference resistance values $R_{ref2, 0, (k\ ppm)}$ (second initial reference immittance values), the measured target resistance value $R_{sen}$, the second measured target resistance value $R_{ref2}$, a plurality of second correlations $F_{2(k\ ppm)}$, and the target gas concentration converting function.

Please refer to FIG. 11B, which illustrates a detailed flowchart of step S94 of FIG. 11A. Please refer to step S941. The controller 70' calculates a plurality of first predicted coefficients of variation $\alpha_{(k\ ppm)}$ (namely the plurality of range reference values as described in the range calculating stage B3) according to the second measured reference resistance value $R_{ref2}$, a plurality of second initial reference resistance values $R_{ref2, 0, (k\ ppm)}$, and a plurality of first correlation functions $F_{1\ (k\ ppm)}$. For example, if the specified concentration values have four values, including 0 ppm, 20 ppm, 100 ppm and 200 ppm, based on these specified concentration values, the controller 70' substitutes each of the quotient values of the second measured reference resistance value $R_{ref2}$ divided by each of the second initial reference resistance values $R_{ref2, 0, (k\ ppm)}$ into each of the first correlation functions $F_{1\ (k\ ppm)}$ to obtain four first predicted coefficients of variation $\alpha_{(k\ ppm)}$, including $\alpha_{(0\ ppm)}$, $\alpha_{(20\ ppm)}$, $\alpha_{(100\ ppm)}$, and $\alpha_{(200\ ppm)}$, as shown in equations 30-33.

$$\alpha_{(0\ ppm)} = F_{1(0\ ppm)}(R_{ref2}/R_{ref2,0,(0\ ppm)}) \quad \text{(Equation 30)}$$

$$\alpha_{(20\ ppm)} = F_{1(20\ ppm)}(R_{ref2}/R_{ref2,20,(20\ ppm)}) \quad \text{(Equation 31)}$$

$$\alpha_{(100\ ppm)} = F_{1(100\ ppm)}(R_{ref2}/R_{ref2,100,(100\ ppm)}) \quad \text{(Equation 32)}$$

$$\alpha_{(200\ ppm)} = F_{1(200\ ppm)}(R_{ref2}/R_{ref2,200,(200\ ppm)}) \quad \text{(Equation 33)}$$

Please refer to step S943. The controller 70' selects one from the plurality of first predicted coefficients of variation $\alpha_{(k\ ppm)}$ according to the first reference coefficient of variation α (namely the comparison baseline value as described in the range comparing stage B5). For example, the controller 70' calculates a plurality of difference values between the first reference coefficient of variation α and each of the plurality of first predicted coefficients of variation $\alpha_{(k\ ppm)}$ and selects the first predicted coefficients of variation $\alpha_{(x\ ppm)}$ corresponding to the minimum one of difference values (or the minimum one of the absolute difference values) and the concentration value x corresponding to the first predicted coefficients of variation $\alpha_{(x\ ppm)}$.

Please refer to step S945. The controller 70' calculates the target coefficient of variation $\beta_{(x\ ppm)}$ according to the first predicted coefficients of variation $\alpha_{(x\ ppm)}$, and the second correlation functions $F_{2\ (x\ ppm)}$.

The first predicted coefficients of variation $\alpha_{(x\ ppm)}$ selected in step S943 and the second correlation functions $F_{2\ (x\ ppm)}$ correspond to the same concentration value x. Regarding the calculation approach of the target coefficient of variation $\beta_{(x\ ppm)}$, for example, the controller 70' selects one from the quotient values calculated in step S941 to be substituted into the second correlations $F_{2\ (k\ ppm)}$ with corresponding specified concentration value to obtain the target coefficient of variation $\beta_{(x\ ppm)}$ as shown in equation 34 below.

$$\beta_{(k\ ppm)} = F_{2(k\ ppm)}(R_{ref2}/R_{ref2,0,(k\ ppm)}) \quad \text{(Equation 34)}$$

Please refer to step S947. The controller 70' calculates the calibration resistance value $R_{cal}$ (calibration immittance value) according to the measured target resistance value $R_{sen}$ and the target coefficient of variation $\beta_{(x\ ppm)}$. Regarding the calculation approach of the calibration resistance value $R_{cal}$, for example, the controller 70' uses the quotient value of the measured target resistance value $R_{sen}$ divided by the target coefficient of variation $\beta_{(x\ ppm)}$ as the calibration resistance value $R_{cal}$, as shown in equation 35.

$$R_{cal} = R_{sen}/\beta_{(k\ ppm)} \quad \text{(Equation 35)}$$

Please refer to step S949, the controller 70' substitutes the calibration resistance value $R_{cal}$ into the target gas concentration converting function to obtain the target gas concentration value.

Figure 12A:
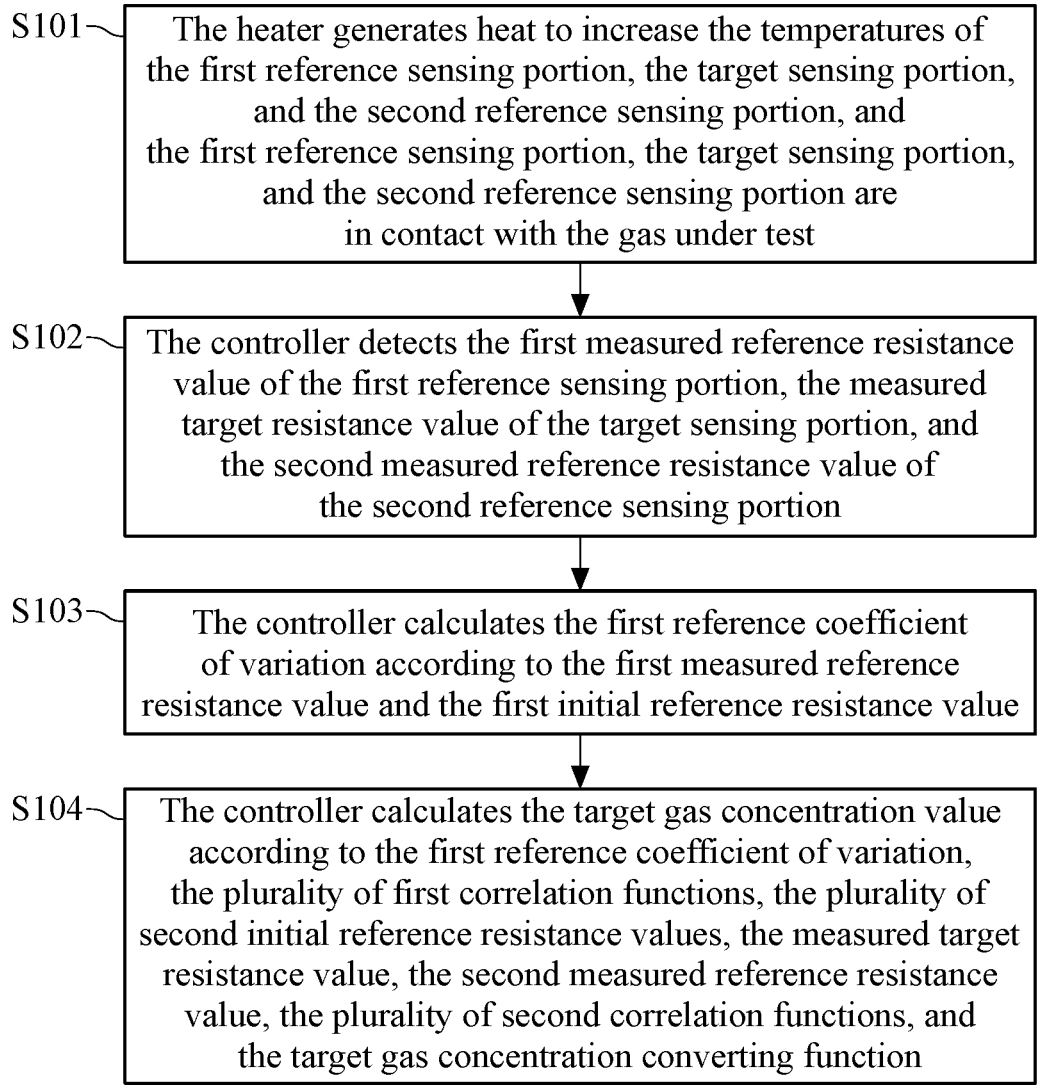
FIG. 12A is a flowchart of the gas concentration sensing method of the fourth example of the present disclosure.
Figure 12B:
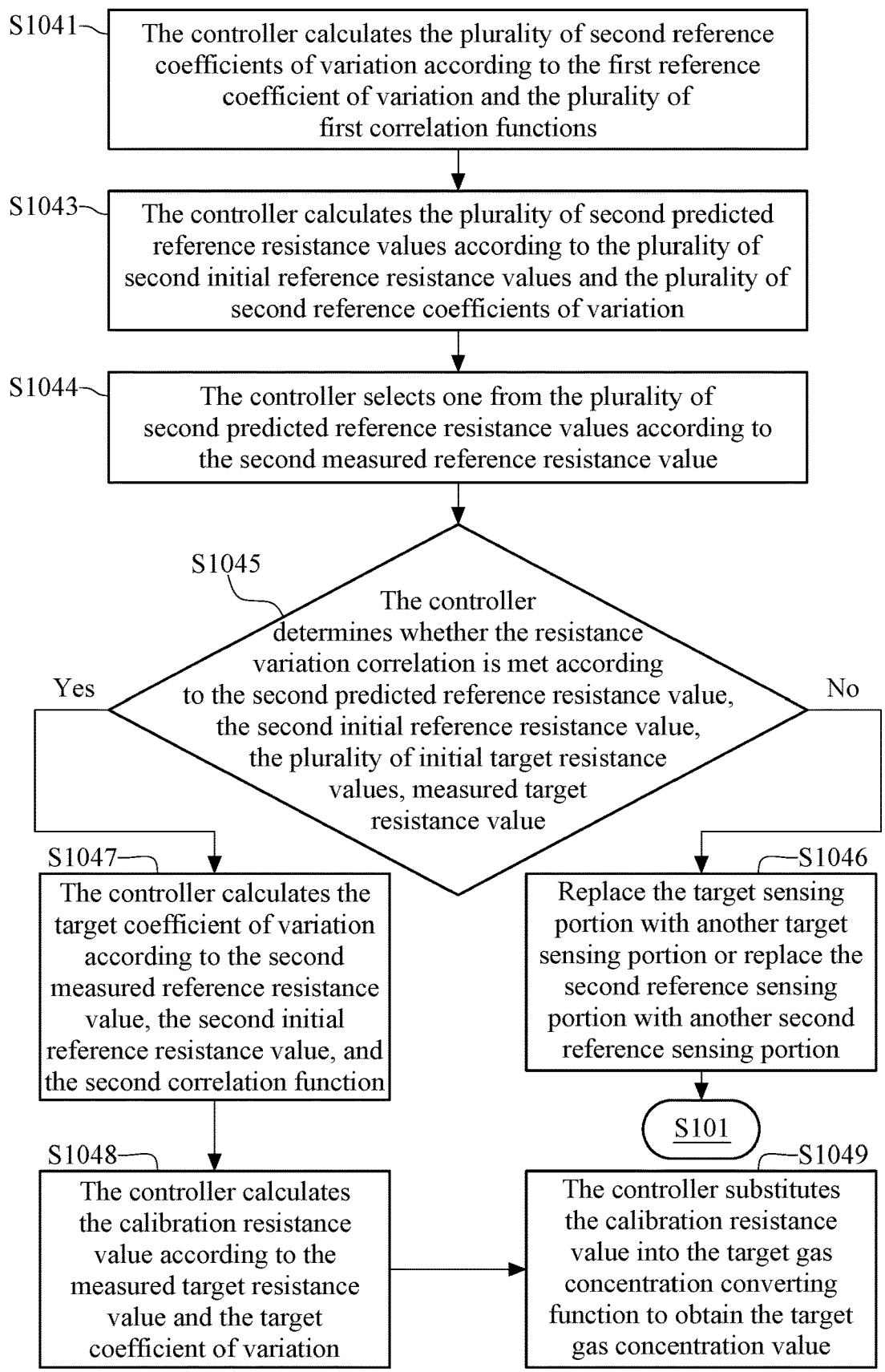
FIG. 12B is a detailed flowchart of step S104.

Please refer to FIGS. 12A and 12B, which illustrate a flowchart and a detailed flowchart of the gas concentration sensing method of the fourth example of the present disclosure. Steps S101-S102 of FIG. 12A belong to the aforementioned immittance obtaining stage B1, steps S103, S1041, and S1043 belong to the aforementioned range calculating stage B3, step S1044 belongs to the aforementioned range comparing stage B5, and step S1047 belongs to the aforementioned concentration calculating stage B7.

Please refer to step S101. The heater 10 generates heat to increase the temperatures of the first reference sensing portion 30, the target sensing portion 40, and the second reference sensing portion 50, and the gas under test is in contact with the above portions 30, 40 and 50.

Please refer to step S102, when the temperatures of the first reference sensing portion 30, the target sensing portion 40, and the second reference sensing portion 50 increase and the above portions 30, 40 and 50 are in contact with the gas under test, the controller 70' detects the first measured reference resistance value $R_{ref1}$ (the first measured reference immittance value) of the first reference sensing portion 30, the measured target resistance value $R_{sen}$ (the measured target immittance value) of the target sensing portion 40, and the second measured reference resistance value $R_{ref2}$ (the second measured reference immittance value) of the second reference sensing portion 50. For example, the controller 70' may detect the first measured reference resistance value $R_{ref1}$ of the first sensing layer 301 through the first conductive layer 303, detect the measured target resistance value $R_{sen}$ of the second sensing layer 401 through the second conductive layer 403, and detect the second measured reference resistance value $R_{ref2}$ of the third sensing layer 501 through the third conductive layer 503.

Please refer to step S103. The controller 70' calculates the first reference coefficient of variation α according to the first measured reference resistance value $R_{ref1}$ and the first initial reference resistance value $R_{ref1, 0}$ (the first initial reference immittance value). The first initial reference resistance value $R_{ref1, 0}$ is associated with the first reference sensing portion 30. For example, before the gas sensing device 200 is shipped, the target gas of specified concentration such as 0 ppm is directed to be contact with the heated first reference sensing portion 30. At this time, the controller 70' detects the resistance value of the first reference sensing portion 30, and then this resistance value is served as the first initial reference resistance value $R_{ref1, 0}$ and is stored in a built-in element of the controller 70' or in a storage device. For example, the first reference coefficient of variation α is a ratio of the first measured reference resistance value $R_{ref1}$ to the first initial reference resistance value $R_{ref1, 0}$ as shown in equation 36. The first reference coefficient of variation α is configured to reflect the degree of the affection of the current environmental variation, such as the unstable absorption of the oxygen, the variation of the humidity, to the first reference sensing portion 30.

$$\alpha = R_{ref1}/R_{ref1,0} \quad \text{(Equation 36)}$$

Please refer to step S104. The controller 70' calculates the target gas concentration value according to the first reference coefficient of variation α, a plurality of first correlation functions $F_{1(k\ ppm)}$, a plurality of second initial reference resistance values $R_{ref2,\ 0,\ (k\ ppm)}$ (second initial reference immittance values), the measured target resistance value $R_{sen}$, the second measured reference resistance value $R_{ref2}$, a plurality of second correlations $F_{2(k\ ppm)}$, and the target gas concentration converting function.

The number of the plurality of first correlation functions $F_{1(k\ ppm)}$, the number of the plurality of second initial reference resistance values $R_{ref2,\ 0,\ (k\ ppm)}$, and the number of the plurality of second correlations $F_{2(k\ ppm)}$ both depend on the number of specified concentration values. For example, if the specified concentration values have four values including 0 ppm, 20 ppm, 100 ppm and 200 ppm, the four corresponding first correlation functions $F_{1\ (k\ ppm)}$ are $F_{1\ (0\ ppm)}$, $F_{1\ (20\ ppm)}$, $F_{1\ (100\ ppm)}$, and $F_{1\ (200\ ppm)}$; the four corresponding second initial reference resistance values $R_{ref2,\ 0,\ (k\ ppm)}$ are $R_{ref2,\ 0,\ (0\ ppm)}$, $R_{ref2,\ 0,\ (20\ ppm)}$, $R_{ref2,\ 0,\ (100\ ppm)}$, and $R_{ref2,\ 0,\ (200\ ppm)}$; and the four corresponding second correlation functions $F_{2(k\ ppm)}$ are $F_{2\ (0\ ppm)}$, $F_{2\ (20\ ppm)}$, $F_{2\ (100\ ppm)}$, and $F_{2\ (200\ ppm)}$. Based on the condition of the target gas of every specified concentration values, each of the plurality of first correlation functions $F_{1\ (k\ ppm)}$ represents a correlation between the first reference sensing portion 30 and the second reference sensing portion 50. For example, the first correlation function $F_{1\ (k\ ppm)}$ represents a dependency relationship between the first measured reference resistance value $R_{ref1}$ and the second measured reference resistance value $R_{ref2}$. For another example, the first correlation function $F_{1\ (k\ ppm)}$ represents a dependency relationship between a variability of the first measured reference resistance value $R_{ref1}$ and a variability of the second measured reference resistance value $R_{ref2}$. Regarding the plurality of second initial reference resistance values $R_{ref2,\ 0,\ (k\ ppm)}$, for example, before the gas sensing device 200 is shipped, the target gases of a plurality of specified concentration values, such as 0 ppm, 20 ppm, 100 ppm, and 200 ppm, are directed to be in contact with the heated second reference sensing portion 50 respectively. At this time, the controller 70' detects the resistance value of the second reference sensing portion 50, such as $R_{ref2,\ 0,\ (0\ ppm)}$, $R_{ref2,\ 0,\ (20\ ppm)}$, $R_{ref2,\ 0,\ (100\ ppm)}$, and $R_{ref2,\ 0,\ (200\ ppm)}$, and then these resistance values are served as the plurality of second initial reference resistance value $R_{ref2,\ 0,\ (k\ ppm)}$ and are stored in a built-in storage element of the controller 70' or in a storage device. Based on the condition of the target gas of every specified concentration values, each of the plurality of second correlation functions $F_{2(k\ ppm)}$ represents a dependency relationship between the second reference sensing portion 50 and the target sensing portion 40. For example, the second correlation functions $F_{2(k\ ppm)}$ represent a dependency relationship between the second measured reference resistance $R_{ref2}$ and the measured target resistance value $R_{sen}$. For another example, the second correlation functions $F_{2(k\ ppm)}$ represent a dependency relationship between a variability of the second measured reference resistance $R_{ref2}$ and a variability of the measured target resistance value $R_{sen}$.

Please refer to FIG. 12B, which illustrates a detailed flowchart of step S104 of FIG. 12A. Please refer to step S1041. The controller 70' calculates the plurality of second reference coefficients of variation $\gamma_{(k\ ppm)}$ according to the first reference coefficient of variation α and the plurality of first correlation functions $F_{1\ (k\ ppm)}$. The number of the second reference coefficients of variation $\gamma_{(k\ ppm)}$ depends on the number of the plurality of first correlation functions $F_{1\ (k\ ppm)}$. Following the previous example, the controller 70' substitutes the first reference coefficient of variation α into four first correlation functions $F_{1\ (k\ ppm)}$ respectively to obtain four second reference coefficients of variation $\gamma_{(k\ ppm)}$, including $\gamma_{(0\ ppm)}$, $\gamma_{(20\ ppm)}$, $\gamma_{(100\ ppm)}$, and $\gamma_{(200\ ppm)}$, as shown in equations 37-40 below.

$$\gamma_{(0\ ppm)} = F_{1(0\ ppm)}(\alpha) \quad \text{(Equation 37)}$$

$$\gamma_{(20\ ppm)} = F_{1(20\ ppm)}(\alpha) \quad \text{(Equation 38)}$$

$$\gamma_{(100\ ppm)} = F_{1(200\ ppm)}(\alpha) \quad \text{(Equation 39)}$$

$$\gamma_{(100\ ppm)} = F_{1(200\ ppm)}(\alpha) \quad \text{(Equation 40)}$$

Please refer to step S1043. The controller 70' calculates a plurality of second predicted reference resistance values $R_{ref2,\ pre,\ (k\ ppm)}$ (second predicted reference immittance values, which is the plurality of range reference values as described in the range calculating stage B3) according to a plurality of second initial reference resistance values $R_{ref2,\ 0,\ (k\ ppm)}$ and the plurality of second reference coefficients of variation $\gamma_{(k\ ppm)}$. Regarding the calculation approach of step S1043, following the previous example, for each of the plurality of specified concentration values, such as 0 ppm, 20 ppm, 100 ppm, and 200 ppm, the product of the second initial reference resistance values $R_{ref2,\ 0,\ (k\ ppm)}$ corresponding one of the plurality of specified concentration values and the second reference coefficients of variation $\gamma_{(k\ ppm)}$ corresponding said one of the plurality of specified concentration values is served as the second predicted reference resistance values $R_{ref2,\ pre,\ (k\ ppm)}$, including $R_{ref2,\ pre,\ (0\ ppm)}$, $R_{ref2,\ pre,\ (20\ ppm)}$, $R_{ref2,\ pre,\ (100\ ppm)}$, and $R_{ref2,\ pre,\ (200\ ppm)}$, as shown in equations 47 and 41-43 below.

$$R_{ref2,pre,(0\ ppm)} = R_{ref20,(0\ ppm)} \cdot \gamma_{(0\ ppm)} \quad \text{(Equation 47)}$$

$$R_{ref2,pre,(20\ ppm)} = R_{ref20,(20\ ppm)} \cdot \gamma_{(20\ ppm)} \quad \text{(Equation 41)}$$

$$R_{ref2,pre,(100\ ppm)} = R_{ref20,(100\ ppm)} \cdot \gamma_{(100\ ppm)} \quad \text{(Equation 42)}$$

$$R_{ref2,pre,(200\ ppm)} = R_{ref20,(200\ ppm)} \cdot \gamma_{(200\ ppm)} \quad \text{(Equation 43)}$$

Please refer to step S1044. The controller 70' selects one from the plurality of second predicted reference resistance values $R_{ref2,\ pre,\ (k\ ppm)}$ according to the second measured reference resistance values $R_{ref2}$ (namely the comparison baseline value as described in the range comparing stage B5). For example, the controller 70' calculates a plurality of difference values between the second measured reference resistance values $R_{ref2}$ and each of the plurality of second predicted reference resistance values $R_{ref2,\ pre,\ (k\ ppm)}$ and selects the second predicted reference resistance value $R_{ref2,\ pre,\ (x\ ppm)}$ corresponding to the minimum one of difference values (or the minimum one of the absolute difference values).

Please refer to step S1045. The controller 70' determines whether the second measured reference resistance value $R_{ref2}$, the second initial reference resistance values $R_{ref2,\ 0,\ (x\ ppm)}$, the measured target resistance value $R_{sen}$, and the one of the plurality of initial target resistance values $R_{sen\ 0,\ (k\ ppm)}$ meet an resistance variation correlation (immittance variation correlation), wherein the specified concentration value x corresponding to both the second initial reference immittance values $R_{ref2,\ 0,\ (x\ ppm)}$ and said one $R_{sen\ 0,\ (x\ ppm)}$ of the plurality of initial target resistance values $R_{sen\ 0,\ (k\ ppm)}$ equals to the specified concentration value x corresponding to the second predicted reference resistance value $R_{ref2,\ pre,\ (x\ ppm)}$. For example, the resistance variation correlation is a dependency relationship between the variation of the resistance values of the second reference sensing portion 50 and the variation of the resistance values of the target sensing portion 40. For another example, the resistance variation correlation is a dependency relationship between the variability of the resistance values of the second reference sensing portion 50 and the variability of the resistance values of the target sensing portion 40. Said variation of the resistance values represents a difference value between the measured resistance value and the initial resistance value. Said variability of the resistance values represents a quotient value of the measured resistance value divided by the initial resistance value. Taking the variability of the resistance values as an example, the controller 70' determines whether the values on both side of the equal sign in the equation 44 are within an error tolerance range as shown in equation 44.

$$(R_{sen}/R_{sen\ 0,(k\,ppm)})-(R_{ref2}/R_{ref2,0,(k\,ppm)})<e \qquad \text{(Equation 44)}$$

In the equation 44, the first ratio is $R_{sen}/R_{sen\ 0,\ (k\,ppm)}$, and the second ratio is $R_{ref2}/R_{ref2,\ 0,\ (k\,ppm)}$.

If the determination result of step S1045 is negative (the immittance variation correlation is not met), namely that one of the target sensing portion 40 and the second reference sensing portion 50 does not work normally, and step S1046 is performed next for replacing with another target sensing portion or another second reference sensing portion. After the step S1046 finishes, step S101 is performed next for re-performing the fourth example of the gas concentration sensing method. If the determination result of step S1045 is positive (the immittance variation correlation is met), step S1047 is performed next.

Please refer to step S1047. The controller 70' calculates the target coefficient of variation $\beta_{(x\,ppm)}$ according to the second measured reference resistance value $R_{ref2}$, the second initial reference resistance values $R_{ref2,\ 0,\ (x\,ppm)}$, and the second correlation functions $F_{2\ (x\,ppm)}$. The target coefficient of variation $\beta_{(x\,ppm)}$ is served as a parameter in the concentration calculating stage B7. The second initial reference resistance values $R_{ref2,\ 0,\ (x\,ppm)}$, the second predicted reference resistance values $R_{ref2,\ 0,\ (x\,ppm)}$ selected in step S1045, and the second correlation functions $F_{2\ (x\,ppm)}$ correspond to the same concentration value x. Regarding the calculation approach of the target coefficient of variation $\beta_{(x\,ppm)}$, for example, the controller 70' uses value obtained based on the second correlation function $F_{2\ (x\,ppm)}$ using the quotient value of the second measured reference resistance value $R_{ref2}$ divided by the second initial reference resistance values $R_{ref2,\ 0,\ (x\,ppm)}$ as input, as shown in equation 45, wherein the quotient value is the target coefficient of variation $\beta_{(x\,ppm)}$.

$$\beta_{(k\,ppm)}=F_{2(k\,ppm)}(R_{ref2}/R_{ref2,0,(k\,ppm)}) \qquad \text{(Equation 45)}$$

Please refer to step S1048. The controller 70' calculates the calibration resistance value $R_{cal}$ (calibration immittance value) according to the measured target resistance value $R_{sen}$ and the target coefficient of variation $\beta_{(x\,ppm)}$. Regarding the calculation approach of the calibration resistance value $R_{cal}$, for example, the controller 70' uses the quotient value of measured target resistance value $R_{sen}$ divided by the target coefficient of variation $\beta_{(x\,ppm)}$ as the calibration resistance value $R_{cal}$, as shown in equation 46.

$$R_{cal}=R_{sen}/\beta_{(k\,ppm)} \qquad \text{(Equation 46)}$$

Please refer to step S1049, the controller 70' substitutes the calibration resistance value $R_{cal}$ into the target gas concentration converting function to obtain the target gas concentration value.

Two examples of the gas concentration sensing method adapted to the first embodiment of the gas sensing device 100 and four examples of the gas concentration sensing method adapted to the second embodiment of the gas sensing device 200 are described above. In the above six examples, after the target gas concentration value is obtained, the controller 70 or 70' may further update a standard curve according to the target gas concentration value and the calibration resistance value $R_{cal}$. The standard curve is a function curve of the target gas concentration converting function.

In practice, before the gas sensing device 100 or 200 is shipped, the present disclosure may detect a plurality of default resistance values (default immittance values) of the target sensing portion 40 in contact with a plurality of specified concentration values. In other words, each of the default immittance values is associated with the target sensing portion 40 and each of the specified concentration values corresponds to one of these default immittance values, and the target gas concentration converting function is associated with these specified concentration values and these default immittance values. The specified concentration values and the default immittance values described above are recorded as Table 1 below. After the gas sensing device 100 or 200 is applied in practice and the target gas concentration value is obtained, the controller 70 or 70' determines that whether the calibration resistance value belongs to one of the updating ranges corresponding to the specified concentrations. If the determination result is positive, the controller 70 or 70' replace the calibration resistance value $R_{cal}$ with said one of the default resistance value corresponding to the specified concentration value. If the determination result is negative, the controller 70 or 70' adds a new row to table 1 with the calibration resistance value $R_{cal}$ the target concentration values.

TABLE 1

| Default resistance value(KΩ) | Specified concentration value(ppm) |
|---|---|
| 4805 | 1.28 |
| 3576 | 25.1 |
| 2107 | 107.1 |
| 1407 | 215.8 |

For example, if the updating range is 5 ppm, the calibration resistance value (calibration immittance value) $R_{cal}$ is 3749 KΩ, and the target concentration value is 22.5 ppm in the $n^{th}$ measurements. In this example, the controller 70 or 70' finds that the entry whose specified concentration value is 25.1 ppm meets the updating requirement (25.1-5<22.5<25.1+5). Therefore, the controller 70 or 70' update the entry whose default resistance value is 3576 KΩ.

Following the previous example, if the calibration resistance value $R_{cal}$ is 2013 KΩ, and the target concentration value is 124.0 ppm in the $(n+1)^{th}$ measurements. In this example, the controller 70 or 70' cannot find an entry whose updating range of specified concentration value contains this calibration value (107.1-5<124.5, however, 107.1+5<124.5). Therefore, the controller 70 or 70' adds (2013, 1024.0) the measured data in a form of "resistance-concentration" into the table 1, and the table 1 is updated to table 2 below according to the above two example.

TABLE 2

| Default resistance value(KΩ) | Specified concentration value(ppm) |
|---|---|
| 4805 | 1.28 |
| 3749 | 25.1 |
| 2107 | 107.1 |
| 2013 | 124.0 |
| 1407 | 215.8 |

Base on the above updating strategy that the controller 70 or 70' updates these default immittance values and selectively update the specified concentration value according to the calibration immittance value, the target gas concentration value, the plurality default immittance values and the updating range, every time the calibration resistance value and calibration concentration value generated by the gas sensing device 100 or 200 can be feedbacked to the standard curve or the table corresponding to the standard curve. The above updating strategy have a dynamic calibrating effect for the gas concentration sensing method of the present disclosure. In addition, when the sensitivity of the sensing material to the target gas has varied, the gas sensing device 100 or 200 may keep to output an accurate target gas concentration value.

Figure 13:
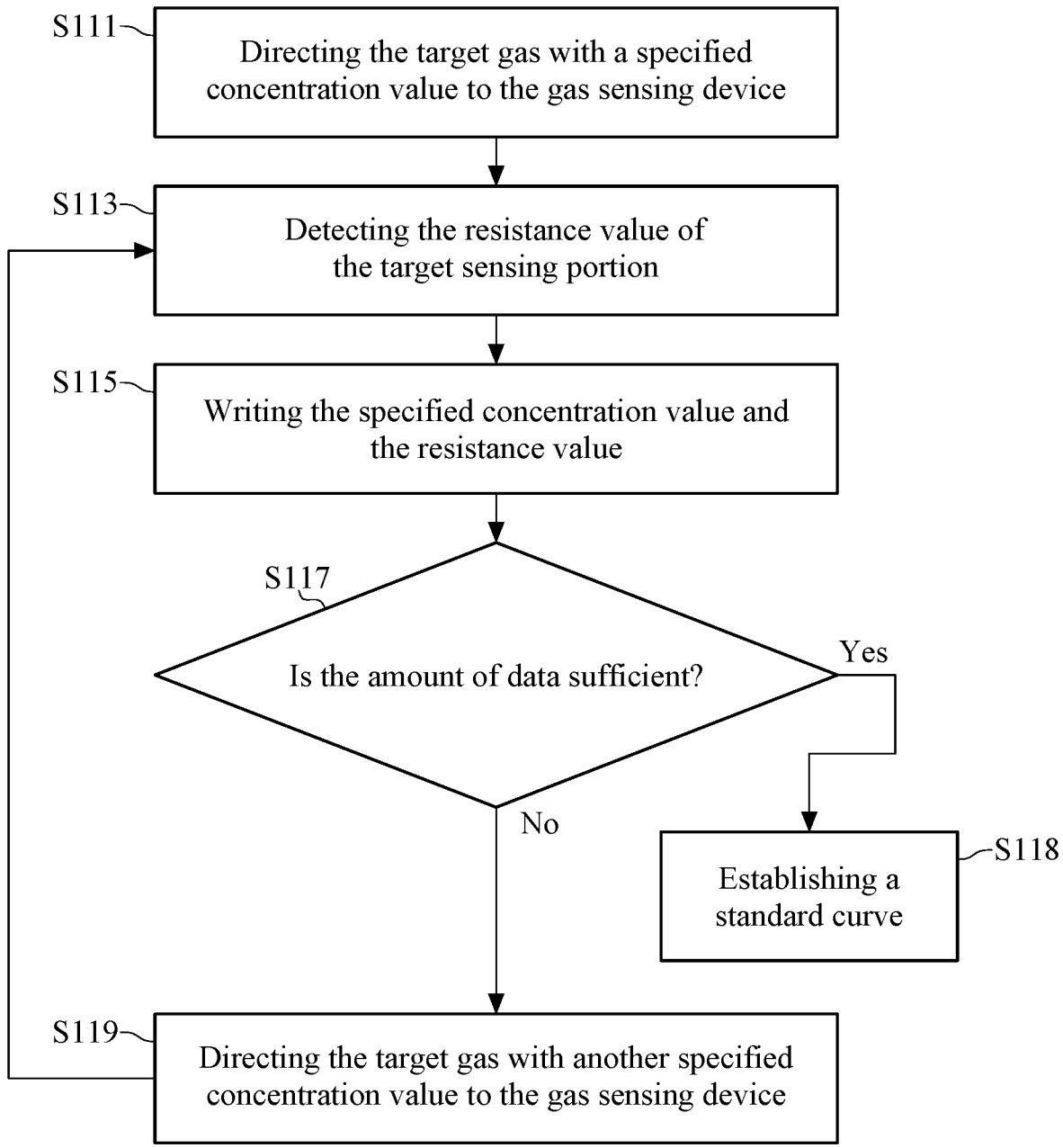
FIG. 13 is a flowchart of the standard curve of establishing the target gas concentration converting function.

Please refer to FIG. 13, which illustrates a flowchart of the standard curve of establishing the target gas concentration converting function.

Please refer to step S111, which shows "directing the target gas with a specified concentration value to the gas sensing device 100 or 200". For example, the target gas whose specified concentration value is 25 ppm is directed to the gas sensing device 100 or 200, and the heater 10 generates heat to increase temperatures of sensing portions 30-60, and the target gas is directed to the gas sensing device 100 or 200.

Please refer to step S113, which shows "detecting the resistance value of the target sensing portion". Specifically, the controller 70 or 70' detected the measured target resistance value $R_{sen}$, such as 3576 KΩ.

Please refer to step S115, which shows "writing the specified concentration value and the resistance value". Specifically, the controller 70 or 70' stores the data (25 ppm, 3576 KΩ) into the built-in storage element of the controller 70 or 70' or into the storage device. This step is to increase the coordinate point.

Please refer to step S117, which shows "determining whether the amount of data is sufficient". Specifically, the controller 70 or 70' determines whether the increased coordinate points is sufficient to establish a standard curve of the target gas concentration converting function. If the determination result is positive, step S118 is performed for establishing a standard curve. If the determination result is negative, step S119 is performed next.

Please refer to step S119, which shows "directing the target gas with another specified concentration value to the gas sensing device 100 or 200". For example, the controller 70 or 70' direct a target gas having a specified concentration value of 100 ppm to the gas sensing device 100 or 200, and then repeats the processes of steps S113 to S117 until the determination result of step S117 is positive, and the establishment of a standard curve of another specified concentration value can be completed.

In view of the above, the present disclosure proposes the gas sensing device and the gas concentration sensing method capable of calibrating automatically uses the reference sensing portion to provide a self-compensation information to the target sensing portion so that the drifting resistance value can be corrected. In addition, the present disclosure can dynamically fix the standard curve established in advance by the gas sensing device according to the resistance value and the concentration value after each correction, so as to provide a more accurate gas concentration sensing result in the next sensing operation. In overall, the present disclosure may effectively calibrate the sensing result and the data outputted by the gas sensing element may provide the information for updating the default data, which means that even the sensitivity of the sensing material of the gas sending device has varied due to factors such as environment, aging, or incomplete burn-in operation, variation may be detected and be calibrated dynamically. Furthermore, even the sensing material is aged or poisoned, the sensitivity variation may be tracked by fixing the standard curve of the sensing material and thus the lifetime of the gas sensing device is extended.

Although the present disclosure is described in the aforementioned embodiments, it is not intended to limit the present disclosure. Changes and modifications made without departing from the spirit and scope of the present disclosure belong to the claims of the present disclosure. For the protection scope defined by the present disclosure, please refer to the attached claims.

What is claimed is:

1. A gas concentration sensing method, adapted to a gas sensing device capable of sensing a concentration of a target gas in a gas under test, wherein the gas sensing device comprises a reference sensing portion, a target sensing portion, and a controller, a sensitivity of the reference sensing portion to the target gas is lower than a sensitivity of the target sensing portion to the target gas, and the gas concentration sensing method comprises:
   detecting a measured reference immittance value of the reference sensing portion and a measured target immittance value of the target sensing portion by the controller when the reference sensing portion and the target sensing portion are in contact with the gas under test;
   calculating a reference coefficient of variation by the controller according to the measured reference immittance value and an initial reference immittance value corresponding to the reference sensing portion; and
   calculating a target gas concentration value by the controller according to the reference coefficient of variation, a correlation function, the measured target immittance value, and a target gas concentration converting function, wherein the correlation function represents a correlation between the reference sensing portion and the target sensing portion.

2. The gas concentration sensing method of claim 1, wherein the gas sensing device further comprises a heater, and the gas concentration sensing method further comprises:
   generating heat by the heater to increase a temperature of the reference sensing portion and a temperature of the target sensing portion before the reference sensing portion and the target sensing portion being in contact with the gas under test.

3. The gas concentration sensing method of claim 1, wherein the reference coefficient of variation is a ratio of the measured reference immittance value to the initial reference immittance value or a difference between the measured reference immittance value and the initial reference immittance value.

4. The gas concentration sensing method of claim 1, wherein the correlation function represents a correlation between a variability of the measured reference immittance value of the reference sensing portion and a variability of the measured target immittance value of the target sensing portion.

5. The gas concentration sensing method of claim 1, wherein calculating the target gas concentration value by the controller according to the reference coefficient of variation, the correlation function, the measured target immittance value, and the target gas concentration converting function comprises:
   substituting the reference coefficient of variation into the correlation function to obtain a target coefficient of variation by the controller;
   calculating a calibration immittance value by the controller according to the measured target immittance value and the target coefficient of variation; and
   substituting the calibration immittance value into the target gas concentration converting function to obtain the target gas concentration value by the controller.

6. The gas concentration sensing method of claim 5 further comprising updating a standard curve corresponding to the target gas concentration converting function by the controller according to the calibration immittance value and the target gas concentration value.

7. A gas concentration sensing method adapted to a gas sensing device capable of sensing a concentration of a target gas in a gas under test, wherein the gas sensing device comprises a reference sensing portion, a target sensing portion, and a controller, a sensitivity of the reference sensing portion to the target gas is lower than a sensitivity of the target sensing portion to the target gas, and the gas concentration sensing method comprises:
   an immittance obtaining stage comprising detecting a measured reference immittance value of the reference sensing portion and a measured target immittance value of the target sensing portion by the controller when the reference sensing portion and the target sensing portion are in contact with the gas under test;
   a range calculating stage comprising calculating a plurality of predicted target immittance values according to the measured reference immittance value and a plurality of correlation functions by the controller, with both the plurality of correlation functions and the plurality of predicted target immittance values corresponding to a plurality of specified concentration values;
   a range comparing stage comprising comparing the measured target immittance value to the plurality of predicted target immittance values by the controller for selecting one of the plurality of specified concentration values; and
   a concentration calculating stage comprising calculating a target gas concentration value according to one of a plurality of target coefficients of variation and the measured target immittance value by the controller, with said one of the plurality of target coefficients of variation corresponding to said one of the plurality of specified concentration values.

8. The gas concentration sensing method of claim 7, wherein the gas sensing device further comprises a heater and the immittance obtaining stage further comprises generating heat by the heater to increases a temperature of the reference sensing portion and a temperature of the target sensing portion.

9. The gas concentration sensing method of claim 7, wherein the range calculating stage comprises:
   calculating a reference coefficient of variation according to the measured reference immittance value and an initial reference immittance value by the controller;
   calculating the plurality of target coefficients of variation according to the reference coefficient of variation and the plurality of correlation functions by the controller; and
   calculating the plurality of predicted target immittance values according to a plurality of initial target immittance values and the plurality of target coefficients of variation by the controller; wherein the initial reference immittance value is associated with the reference sensing portion;
   the plurality of initial target immittance values are associated with the target sensing portion and the plurality of specified concentration values of the target gas; and
   each of the plurality of correlation functions represents a correlation between the reference sensing portion and the target sensing portion in contact with the target gas having one of the plurality of specified concentration values.

10. The gas concentration sensing method of claim 9, wherein the concentration calculating stage comprises:
    calculating a calibration immittance value according to the measured target immittance value and said one of the plurality of target coefficients of variation by the controller; and
    substituting the calibration immittance value into a target gas concentration converting function to obtain the target gas concentration value by the controller.

11. The gas concentration sensing method of claim 10, wherein the target gas concentration converting function is associated with the plurality of specified concentration values and a plurality of default immittance values, each of the plurality of default immittance values is associated with the target sensing portion, and each of the plurality of specified concentration values corresponds to one of the plurality of default immittance values.

12. The gas concentration sensing method of claim 11 further comprising updating the plurality of default immittance values according to the calibration immittance value, the target gas concentration value, the plurality of default immittance values and an updating range by the controller, and selectively updating the plurality of specified concentration value by the controller.

13. A gas concentration sensing method adapted to a gas sensing device capable of sensing a concentration of a target gas in a gas under test, wherein the gas sensing device comprises a first reference sensing portion, a second reference sensing portion, a target sensing portion, and a controller, both a sensitivity of the first reference sensing portion to the target gas and a sensitivity of the second reference sensing portion to the target gas are lower than a sensitivity of the target sensing portion to the target gas, and the gas concentration sensing method comprises:
    an immittance obtaining stage comprising detecting a first measured reference immittance value of the first reference sensing portion, a second measured reference immittance value of the second reference sensing portion, and a measured target immittance value of the target sensing portion by the controller when the reference sensing portions and the target sensing portion are in contact with the gas under test;
    a range calculating stage comprising calculating a plurality of range reference values according to at least one of the first measured reference immittance value, the second measured reference immittance value, and a plurality of correlation functions by the controller, with both the plurality of correlation functions and the plurality of range reference values corresponding to a plurality of specified concentration values;
a range comparing stage comprising comparing the plurality of range reference values to a comparison baseline value by the controller for selecting one of the plurality of specified concentration values; and
a concentration calculating stage comprising calculating a target gas concentration value according to a target coefficient of variation and the measured target immittance value by the controller, with the target coefficient of variation corresponding to said one of the plurality of specified concentration values.

14. The gas concentration sensing method of claim 13, wherein the gas sensing device further comprises a heater and the immittance obtaining stage further comprises generating heat by the heater to increase a temperature of the first reference sensing portion, a temperature of the second reference sensing portion and a temperature of the target sensing portion.

15. The gas concentration sensing method of claim 13, wherein the range calculating stage comprises:
calculating a first reference coefficient of variation according to the first measured reference immittance value and a first initial reference immittance value by the controller;
calculating a plurality of second reference coefficients of variation according to the first reference coefficient of variation and a plurality of first correlation functions by the controller; and
calculating a plurality of second predicted reference immittance values according to a plurality of second initial reference immittance values and the plurality of second reference coefficients of variation by the controller; wherein
the first initial reference immittance value is associated with the first reference sensing portion;
the plurality of second initial reference immittance values is associated with the second reference sensing portion and the plurality of specified concentration values of the target gas; and
the plurality of first correlation functions is the plurality of correlation functions, and each of the plurality of first correlation functions represents a correlation between the first reference sensing portion and the second reference sensing portion in contact with the target gas having one of the plurality of specified concentration values.

16. The gas concentration sensing method of claim 15, wherein the comparison baseline value is the second measured reference immittance value and the plurality of range reference values is the plurality of second predicted reference immittance values.

17. The gas concentration sensing method of claim 16, wherein the concentration calculating stage comprises:
calculating the target coefficient of variation according to the second measured reference immittance value, one of the plurality of second initial reference immittance values, and one of a plurality of second correlation functions by the controller;
calculating a calibration immittance value according to the measured target immittance value and the target coefficient of variation by the controller; and
substituting the calibration immittance value into a target gas concentration converting function to obtain the target gas concentration value by the controller; wherein the plurality of second initial reference immittance values is associated with the second reference sensing portion and the plurality of specified concentration values of the target gas;
each of the plurality of second correlation functions represents a correlation between the second reference sensing portion and the target sensing portion in contact with the target gas having one of the plurality of specified concentration values; and
the specified concentration value corresponding to both said one of the plurality of second initial reference immittance values and said one of the plurality of second correlation functions equals to said one of the plurality of specified concentration values selected by the controller in the range comparing stage.

18. The gas concentration sensing method of claim 17, wherein the concentration calculating stage comprises:
determining whether the second measured reference immittance value, said one of the plurality of second initial reference immittance values, the measured target immittance value, and one of a plurality of initial target immittance values meet an immittance variation correlation by the controller; wherein
when the controller determines that the immittance variation correlation is not met, selectively replacing the target sensing portion with another target sensing portion or replacing the second reference sensing portion with another second reference sensing portion;
when the controller determines that the immittance variation correlation is met, calculating the target coefficient of variation according to the second measured reference immittance value, said one of the plurality of second initial reference immittance values, and said one of the plurality of second correlation functions by the controller; wherein
the plurality of initial target immittance values are associated with the target sensing portion and the plurality of specified concentration values of the target gas and
the specified concentration value corresponding to said one of the plurality of initial target immittance values equals to said one of the plurality of specified concentration values selected by the controller in the range comparing stage.

19. The gas concentration sensing method of claim 18, wherein determining whether the second measured reference immittance value, said one of the plurality of second initial reference immittance values, the measured target immittance value, and said one of a plurality of initial target immittance values meet the immittance variation correlation by the controller comprises:
calculating a first ratio of the measured target immittance value to said one of the plurality of initial target immittance values by the controller;
calculating a second ratio of the second measured reference immittance value to said one of the plurality of second initial reference immittance values by the controller; and
calculating a difference between the first ratio and the second ratio by the controller, and determining whether the immittance variation correlation is met depending on whether the difference is within an error tolerance range.

20. The gas concentration sensing method of claim 13, wherein the range calculating stage comprises:
calculating a plurality of second predicted reference immittance values according to the first measured reference immittance value and a plurality of first correlation functions by the controller, wherein the plurality of first correlation functions are the plurality of correlation functions, and each of the plurality of first correlation functions represents a correlation between the first reference sensing portion and the second reference sensing portion in contact with the target gas having one of the plurality of specified concentration values.

21. The gas concentration sensing method of claim 20, wherein the comparison baseline value is the second measured reference immittance value, and the plurality of range reference values is the plurality of second predicted reference immittance values.

22. The gas concentration sensing method of claim 21, wherein the concentration calculating stage comprises:
calculating the target coefficient of variation according to the second measured reference immittance value, one of a plurality of second initial reference immittance values, and one of a plurality of second correlation functions by the controller;
calculating a calibration immittance value according to the measured target immittance value and the target coefficient of variation by the controller; and
substituting the calibration immittance value into a target gas concentration converting function to obtain the target gas concentration value by the controller; wherein
the plurality of second initial reference immittance values is associated with the second reference sensing portion and the plurality of specified concentration values of the target gas;
each of the plurality of second correlation functions represents a correlation between the second reference sensing portion and the target sensing portion in contact with the target gas having one of the plurality of specified concentration values; and
the specified concentration value corresponding to both said one of the plurality of second initial reference immittance values and said one of the plurality of second correlation functions equals to said one of the plurality of specified concentration values selected by the controller in the range comparing stage.

23. The gas concentration sensing method of claim 13, wherein the range calculating stage comprises:
calculating a plurality of first predicted coefficients of variation according to the second measured reference immittance value, a plurality of second initial reference immittance values, and a plurality of first correlation functions by the controller; wherein the plurality of second initial reference immittance values is associated with the second reference sensing portion and the plurality of specified concentration values of the target gas; and
the plurality of first correlation functions are the plurality of correlation functions, and each of the plurality of first correlation functions represents a correlation between the first reference sensing portion and the second reference sensing portion in contact with the target gas having one of the plurality of specified concentration values.

24. The gas concentration sensing method of claim 23, wherein the range comparing stage comprises:
calculating a first reference coefficient of variation according to the first measured reference immittance value and a first initial reference immittance value by the controller; and
selecting one of the plurality of first predicted coefficients of variation according to the first reference coefficient of variation by the controller; wherein
the first initial reference immittance value is associated with the first reference sensing portion;
the first reference coefficient of variation is the comparison baseline value; and
the plurality of first predicted coefficients of variation is the plurality of range reference values.

25. The gas concentration sensing method of claim 24, wherein the concentration calculating stage comprises:
calculating the target coefficient of variation according to said one selected from the plurality of first predicted coefficients of variation and one of a plurality of second correlation functions by the controller;
calculating a calibration immittance value according to the measured target immittance value and the target coefficient of variation by the controller; and
substituting the calibration immittance value into a target gas concentration converting function to obtain the target gas concentration value by the controller; wherein
each of the plurality of second correlation functions represents a correlation between the second reference sensing portion and the target sensing portion in contact with the target gas having one of the plurality of specified concentration values; and
the specified concentration value corresponding to said one of the plurality of second correlation functions equals to said one of the plurality of specified concentration values selected by the controller in the range comparing stage.

26. A gas sensing device capable of sensing a concentration of a target gas in a gas under test comprising:
a dielectric layer disposed on a surface, wherein the dielectric layer has a supporting side facing away from the surface;
a reference sensing portion disposed on the supporting side, wherein the reference sensing portion comprises a first sensing layer and a first conductive layer;
a target sensing portion disposed on the supporting side, wherein the target sensing portion comprises a second sensing layer and a second conductive layer; and
a controller electrically connecting to the first conductive layer and the second conductive layer, wherein the controller detects a measured reference immittance value of the first conductive layer and a measured target immittance value of the second conductive layer and calculates a target gas concentration value of the target gas according to an initial reference immittance value of the reference sensing portion, a correlation function associated with the reference sensing portion and the target sensing portion, the measured reference immittance value and the measured target immittance value;
wherein a sensitivity of the reference sensing portion to the target gas is lower than a sensitivity of the target sensing portion to the target gas.

27. The gas sensing device of claim 26, wherein the reference sensing portion is a first reference sensing portion, the measured reference immittance value is a first measured reference immittance value, and the gas sensing device further comprises:
a second reference sensing portion disposing on the supporting side, wherein the second reference sensing portion comprises a third conductive layer and a third sensing layer, and the third sensing layer is sensitive to the target gas; and the controller further electrically connects to the third conductive layer, detects a second measured reference immittance value of the third conductive layer, and calculates the target gas concentration value according to the first measured reference immittance value and the second measured reference immittance value.

28. The gas sensing device of claim 27, wherein the target sensing portion is a first target sensing portion, the measured target immittance value is a first measured target immittance value, and the gas sensing device further comprises:
a second target sensing portion disposing on the supporting side, wherein the second target sensing portion comprises a fourth conductive layer and a fourth sensing layer, and the fourth sensing layer is sensitive to the target gas; and
the controller further electrically connects to the fourth conductive layer, detects a second measured target immittance value of the fourth conductive layer, and calculates the target gas concentration value according to one of the first measured target immittance value and the second measured target immittance value.

* * * * *